US 6,555,346 B1

(12) United States Patent
Kretzdorn et al.

(10) Patent No.: US 6,555,346 B1
(45) Date of Patent: Apr. 29, 2003

(54) PROTEIN EXPRESSION IN BACULOVIRUS VECTOR EXPRESSION SYSTEMS

(75) Inventors: Dietmar Kretzdorn, Leichlingen (DE); Dirk Franciscus Marinus van de Wiel, Hardewijk (NL); Abraham Johannes de Smit, Dronten (NL); Robertus Jacobus Maria Moormann, Dronten (NL); Erik Kees Hamann, Lelystad (NL)

(73) Assignees: Stichting Instituut voor Dierhouderij en Diergezondheid, Lelystad (NL); Bayer AG, Leverkussen (NL)

( * ) Notice: Subject to any disclaimer, the term of this patent is extended or adjusted under 35 U.S.C. 154(b) by 0 days.

(21) Appl. No.: 09/596,105

(22) Filed: Jun. 16, 2000

Related U.S. Application Data

(63) Continuation of application No. PCT/NL98/00717, filed on Dec. 17, 1998.

(30) Foreign Application Priority Data

Dec. 18, 1997 (EP) ............................................. 97203989

(51) Int. Cl.$^7$ ............................. C12P 1/04; A61K 39/12
(52) U.S. Cl. .................. 435/71.1; 435/235.1; 435/70.1; 435/71.2; 424/199.1; 424/220.1; 424/204.1; 424/278.1; 530/300; 530/350; 530/399
(58) Field of Search ............................. 435/235.1, 70.1, 435/71.2, 71.1; 424/199.1, 220.1, 204.1, 278.1; 530/300, 350, 399

(56) References Cited

FOREIGN PATENT DOCUMENTS

| EP | 0 389 034 | | 12/1990 |
|---|---|---|---|
| EP | WO96/19498 | * | 6/1996 |
| NL | WO96/25496 | * | 8/1996 |
| WO | WO 95/35380 | | 6/1995 |
| WO | WO 99/31257 | | 12/1998 |

OTHER PUBLICATIONS

Bruschke et al., A subunit vaccine based on glycoprotein E2 of bovine virus diarrhea virus induces fetal protection in sheep against homologous challenge, Vaccine, 15: 1940–1945 (1997).*
Wang et al, Low Multiplicity Infection of Insect Cells with a Recombinant Baculovirus: The Cell Yield Concept, Biotechnology and Bioengineering, vol. 49, pp. 659–666 (1996).*
Hulst et al, Classical swine fever virus diagnostics and vaccine production in insect cells, Cytotechnology, vol. 20, pp. 271–279, 1996.*
Moser, Christian, et al., "Detection of Antibodies Against Classical Swine Fever Virus in Swine Sera by Indirect ELISA Using Recombinant Envelope Glycoprotein E2," Veterinary Microbiology 51, pp. 41–53, 1996.

van Rijn, P.A., et al., "Classical Swine Fever Virus (CSFV) Envelope Glycoprotein E2 Containing One Structural Antigenic Unit Protects Pigs from Lethal CSFV Challenge," Journal of General Virology 77, pp. 2737–2745, 1996.
Hulst, M.M., et al., "Glycoprotein E1 of Hog Cholera Virus Expressed in Insect Cells Protects Swine from Hog Cholera," Journal of Virology, pp. 5435–5442, Sep. 1993.
Ruggli, Nicolas, et al., "Baculovirus Expression and Affinity Purification of Protein E1 of Classical Swine Fever Virus Strain Alfort/187," Virus Genes 10:2, pp. 115–126, 1995.
Hulst, Marcel M., et al., "Glycoprotein E2 of Classical Swine Fever Virus: Expression in Insect Cells and Identification as a Ribonuclease," Virology 200, pp. 558–565, 1994.
Kweon, Chang–Hee, et al., "Expression of Envelope Protein (E2) of Bovine Viral Diarrhea Virus in Insect Cells," J. Vet. Med. Sci. 59(5), pp. 415–419, 1997.
Reddy, J.R., et al., "Application of Recombinant Bovine Viral Diarrhea Virus Proteins in the Diagnosis of Bovine Viral Diarrhea Infection in Cattle," Veterinary Microbiology 51, pp. 119–133, 1997.
Petric, Martin, et al., "Baculovirus Expression of Pestivirus Non–Structural Proteins," Journal of General Virology 73, pp. 1867–1871, 1992.
Chen, Liping, et al., "Coexpression of Cytochrome P4502A6 and Human NADPH–P450 Oxidoreductase in the Baculovirus System," Drug Metabolism and Disposition 25:4, pp. 399–405, 1997.
Radford, Kathryn M., et al., "The Indirect Effects of Multiplicity of Infection on Baculovirus Expressed Proteins in Insects Cells: Secreted and Non–Secreted Products," Cytotechnology 24, pp. 73–81, 1997.
Wu, Jianyong, et al., "Recombinant Protein Production in Insect Cell Cultures Infected with a Temperature–Sensitive Baculovirus," Cytotechnology 9, pp. 141–147, 1992.

(List continued on next page.)

Primary Examiner—Hankyel T. Park
Assistant Examiner—Stacy S. Brown
(74) Attorney, Agent, or Firm—TraskBritt

(57) ABSTRACT

The invention relates to a method to increase protein expression in baculo vector virus expression systems. The invention provides a method to produce a recombinant protein in insect-cell culture which comprises selecting a recombinant baculovirus expressing said protein, growing insect cells in growth medium in a culture vessel and infecting the cells with an inoculum of at least one baculovirus at a cell density of $1 \times 10^5$ to $5 \times 10^6$ cells/ml with an m.o.i of <0.01. The invention furthermore provides a method to produce recombinant pestivirus E2 or $E^{rns}$ protein or fragments thereof in insect cell culture characterized by a final concentration of said protein (fragments) in the growth medium at harvest of at least 100 μg/ml. The invention furthermore provides a method to produce recombinant follicle stimulating hormone, α-units an/or β-units and complexes and fragments thereof, at a concentration in the growth medium at harvest of at least 15 μl.

14 Claims, 14 Drawing Sheets

OTHER PUBLICATIONS

Nguyen, Binh, et al., "Fed–Batch Culture of Insect Cells: A Method to Increase the Yield of Recombinant Human Nerve Growth Factor (rhNGF) in the Baculovirus Expression System," *Journal of Biotechnology 31*, pp. 205–217, 1993.

King, G., et al., "Assessment of Virus Production and Chloramphenicol Acetyl Transferase Expression of Insect Cells in Serum–Free and Serum–Supplemented Media Using a Temperature–Sensitive Baculovirus," *Biotechnology and Engineering 38*, pp. 1091–1099, Nov. 1991.

* cited by examiner

FIG. 1

Shake flask No. 2

| Time (hpi) | Living (#/ml) | Dead (#/ml) | Total (#/ml) | Viability (%) | Living inf (#/ml) | Dead inf (#/ml) | Inf (%) | E2-content (µg/ml) |
|---|---|---|---|---|---|---|---|---|
| -1 | $0.612*10^6$ | $0.018*10^6$ | $0.630*10^6$ | 97.1 | 0 | 0 | 0.0 | 0.0 |
| 20.75 | $1.305*10^6$ | $0.048*10^6$ | $1.353*10^6$ | 96.5 | 0 | 0 | 0.0 | 0.0 |
| 44.25 | $2.030*10^6$ | $0.110*10^6$ | $2.140*10^6$ | 94.9 | 0 | 0 | 0.0 | 0.0 |
| 94.75 | $2.125*10^6$ | $0.415*10^6$ | $2.540*10^6$ | 83.7 | $0.715*10^6$ | $0.395*10^6$ | 43.7 | 96.8 |
| 115 | $1.145*10^6$ | $1.610*10^6$ | $2.755*10^6$ | 41.6 | $0.585*10^6$ | $1.550*10^6$ | 77.5 | 171.0 |
| 139 | $0.608*10^6$ | $2.168*10^6$ | $2.776*10^6$ | 21.9 | $0.364*10^6$ | $2.136*10^6$ | 90.1 | 193.5 |
| 164.5 | Sampling only, no cell count | | | | | | | 176.9 |
| 191 | $0.072*10^6$ | $2.540*10^6$ | $2.612*10^6$ | 2.8 | $0.072*10^6$ | $2.540*10^6$ | 100.0 | 176.4 |
| 215 | Sampling only, no cell count | | | | | | | 136.3 |
| 288 | Sampling only, no cell count | | | | | | | 102.0 |
| 306.5 | Sampling only, no cell count | | | | | | | 96.6 |

Shake flask No. 3

| Time (hpi) | Living (#/ml) | Dead (#/ml) | Total (#/ml) | Viability (%) | Living inf (#/ml) | Dead inf (#/ml) | Inf (%) | E2-content (µg/ml) |
|---|---|---|---|---|---|---|---|---|
| -1 hpi | $0.736*10^6$ | $0.024*10^6$ | $0.760*10^6$ | 96.8 | 0 | 0 | 0.0 | 0.0 |
| 20.75 | $1.179*10^6$ | $0.045*10^6$ | $1.224*10^6$ | 96.3 | 0 | 0 | 0.0 | 0.0 |
| 44.25 | $2.075*10^6$ | $0.085*10^6$ | $2.160*10^6$ | 96.1 | 0 | 0 | 0.0 | 0.0 |
| 94.75 | $1.815*10^6$ | $0.525*10^6$ | $2.340*10^6$ | 77.6 | $0.475*10^6$ | $0.485*10^6$ | 41.0 | 101 |
| 115 | $1.285*10^6$ | $1.510*10^6$ | $2.795*10^6$ | 46.0 | $0.615*10^6$ | $1.425*10^6$ | 73.0 | 196 |
| 139 | $1.060*10^6$ | $3.420*10^6$ | $4.480*10^6$ | 23.7 | $0.584*10^6$ | $3.380*10^6$ | 88.5 | 233 |
| 164.5 | Sampling only, no cell count | | | | | | | 204 |
| 191 | $0.104*10^6$ | $2.692*10^6$ | $2.796*10^6$ | 3.7 | $0.104*10^6$ | $2.692*10^6$ | 100.0 | 212 |
| 215 | Sampling only, no cell count | | | | | | | 141 |
| 288 | Sampling only, no cell count | | | | | | | N.D. |
| 306.5 | Sampling only, no cell count | | | | | | | N.D. |

N.D. = not determined

*FIG. 3A*

Shake flask No. 1 MOI = 0

| Time | 0 hpi | 23 hpi | 95 hpi | 125 hpi | 144 hpi | 173 hpi | 194 hpi |
|---|---|---|---|---|---|---|---|
| Living cells/ml | $4.12*10^5$ | $8.91*10^5$ | $2.36*10^6$ | $2.57*10^6$ | $2.43*10^6$ | $2.51*10^6$ | $2.01*10^6$ |
| Dead cells/ml | $1.6*10^4$ | $2.10*10^4$ | $1.80*10^5$ | $2.70*10^5$ | $3.65*10^5$ | $7.50*10^5$ | $1.09*10^6$ |
| Total cells/ml | $4.28*10^5$ | $9.12*10^5$ | $2.54*10^6$ | $2.84*10^6$ | $2.79*10^6$ | $3.26*10^6$ | $3.09*10^6$ |
| Viability (%) | 96.3 | 97.7 | 92.9 | 90.5 | 86.9 | 77.0 | 64.9 |
| Living inf cells/ml | 0 | 0 | 0 | 0 | 0 | 0 | 0 |
| Dead infected/ml | 0 | 0 | 0 | 0 | 0 | 0 | 0 |
| Total infected cells/ml | 0 | 0 | 0 | 0 | 0 | 0 | 0 |
| Infection (%) | 0 | 0 | 0 | 0 | 0 | 0 | 0 |
| E2 - content (μg/ml) | N.D. | N.D. | N.De. | N.D. | N.D. | N.D. | N.D. |

N.D. = not determined
N.De - not detectable

Shake flask No. 2 MOI = 0.000001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $9.75*10^5$ | $2.67*10^6$ | $2.34*10^6$ | $1.91*10^6$ | $8.60*10^5$ | $5.65*10^5$ |
| Dead cells/ml | $1.3*10^4$ | $2.40*10^4$ | $9.00*10^4$ | $4.50*10^5$ | $9.30*10^5$ | $2.03*10^5$ | $2.30*10^6$ |
| Total cells/ml | $4.35*10^5$ | $9.99*10^5$ | $2.76*10^6$ | $2.79*10^6$ | $2.84*10^6$ | $2.89*10^6$ | $2.86*10^6$ |
| Viability (%) | 97.3 | 97.6 | 96.7 | 83.9 | 67.2 | 29.8 | 19.8 |
| Living inf cells/ml | 0 | 0 | 0 | $9.00*10^4$ | $4.95*10^5$ | $3.85*10^5$ | $3.45*10^5$ |
| Dead infected/ml | 0 | 0 | 0 | $6.00*10^4$ | $4.50*10^5$ | $1.34*10^6$ | $1.89*10^6$ |
| Total infected cells/ml | 0 | 0 | 0 | $1.50*10^5$ | $9.45*10^5$ | $1.72*10^6$ | $2.24*10^6$ |
| Infection (%) | 0 | 0 | 0 | 5.4 | 33.3 | 59.5 | 78.1 |
| E2 - content (μg/ml) | N.D. | N.D. | 1.4 | 19.4 | 49.8 | 107.5 | 144.8 |

Shake flask No. 3 MOI = 0.00001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $7.95*10^5$ | $2.31*10^6$ | $1.67*10^6$ | $1.31*10^6$ | $6.40*10^5$ | $3.00*10^5$ |
| Dead cells/ml | $1.3*10^4$ | $2.70*10^4$ | $9.50*10^4$ | $7.70*10^5$ | $1.29*10^5$ | $1.74*10^6$ | $1.96*10^6$ |
| Total cells/ml | $4.35*10^5$ | $8.22*10^5$ | $2.40*10^6$ | $2.44*10^6$ | $2.59*10^6$ | $2.38*10^6$ | $2.26*10^6$ |
| Viability (%) | 97.3 | 96.7 | 96.0 | 68.4 | 50.4 | 26.9 | 13.3 |
| Living inf cells/ml | 0 | 0 | $1.35*10^5$ | $4.80*10^5$ | $4.85*10^5$ | $3.80*10^5$ | $2.50*10^5$ |
| Dead infected/ml | 0 | 0 | $4.00*10^4$ | $4.85*10^5$ | $9.35*10^5$ | $1.43*10^6$ | $1.85*10^6$ |
| Total infected cells/ml | 0 | 0 | $1.75*10^5$ | $9.65*10^5$ | $1.42*10^6$ | $1.81*10^6$ | $2.10*10^5$ |
| Infection (%) | 0 | 0 | 7.3 | 39.5 | 54.8 | 76.2 | 92.9 |
| E2 - content (μg/ml) | N.D. | N.D. | 24.6 | 100.7 | 135.1 | 177.5 | 195.7 |

Shake flask No. 4 MOI = 0.0001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $7.50*10^5$ | $1.35*10^6$ | $6.65*10^5$ | $2.40*10^5$ | N.D. | N.D. |
| Dead cells/ml | $1.3*10^4$ | $1.80*10^4$ | $1.75*10^5$ | $8.95*10^5$ | $1.36*10^6$ | N.D. | N.D. |
| Total cells/ml | $4.35*10^5$ | $7.68*10^5$ | $1.52*10^6$ | $1.56*10^6$ | $1.60*10^6$ | N.D. | N.D. |
| Viability (%) | 97.3 | 97.7 | 88.5 | 42.6 | 15.0 | N.D. | N.D. |
| Living inf cells/ml | 0 | 0 | $1.01*10^6$ | $6.15*10^5$ | $2.20*10^5$ | N.D. | N.D. |
| Dead infected/ml | 0 | 0 | $1.60*10^5$ | $8.90*10^5$ | $1.36*10^6$ | N.D. | N.D. |
| Total infected cells/ml | 0 | 0 | $1.17*10^6$ | $1.51*10^6$ | $1.58*10^6$ | N.D. | N.D. |
| Infection (%) | 0 | 0 | 76.6 | 96.5 | 98.4 | N.D. | N.D. |
| E2 - content (μg/ml) | N.D. | N.D. | 140.5 | 200.4 | 216.6 | 215.7 | 212.2 |

FIG. 3B

Shake flask No. 5  MOI = 0.001

| Time | 0 hpi | 23 hpi | 95 hpi | 125 hpi | 144 hpi | 173 hpi | 194 hpi |
|---|---|---|---|---|---|---|---|
| Living cells/ml | $4.34*10^5$ | $4.89*10^5$ | $7.60*10^5$ | $4.90*10^5$ | $1.25*10^5$ | N.D. | N.D. |
| Dead cells/ml | $0.8*10^4$ | $2.70*10^4$ | $1.60*10^5$ | $8.55*10^5$ | $7.30*10^5$ | N.D. | N.D. |
| Total cells/ml | $4.42*10^5$ | $5.16*10^5$ | $9.20*10^5$ | $1.35*10^6$ | $8.55*10^5$ | N.D. | N.D. |
| Viability (%) | 98.2 | 94.8 | 82.6 | 36.4 | 14.6 | N.D. | N.D. |
| Living inf cells/ml | 0 | 0 | $7.05*10^5$ | $4.60*10^5$ | $1.25*10^5$ | N.D. | N.D. |
| Dead infected/ml | 0 | 0 | $1.55*10^5$ | $8.55*10^5$ | $7.30*10^4$ | N.D. | N.D. |
| Total infected cells/ml | 0 | 0 | $8.60*10^5$ | $1.32*10^6$ | $8.55*10^5$ | N.D. | N.D. |
| Infection (%) | 0 | 0 | 93.5 | 97.8 | 100.0 | N.D. | N.D. |
| E2 - content (µg/ml) | N.D. | N.D. | 170.6 | 185.7 | 187.9 | 184.5 | 133.3 |

Shake flask No. 6  MOI = 0

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $7.05*10^5$ | $2.52*10^6$ | N.D. | N.D. | N.D. | N.D. |
| Dead cells/ml | $1.3*10^4$ | $4.50*10^4$ | $1.65*10^5$ | N.D. | N.D. | N.D. | N.D. |
| Total cells/ml | $4.35*10^5$ | $7.50*10^5$ | $2.68*10^6$ | N.D. | N.D. | N.D. | N.D. |
| Viability (%) | 97.3 | 94 | 93.8 | N.D. | N.D. | N.D. | N.D. |
| Living inf cells/ml | 0 | 0 | 0 | N.D. | N.D. | N.D. | N.D. |
| Dead infected/ml | 0 | 0 | 0 | N.D. | N.D. | N.D. | N.D. |
| Total infected cells/ml | 0 | 0 | 0 | N.D. | N.D. | N.D. | N.D. |
| Infection (%) | 0 | 0 | 0 | N.D. | N.D. | N.D. | N.D. |
| E2 - content (µg/ml) | N.D. | N.D. | N.De | N.D. | N.D. | N.D. | N.D. |

Shake flask No. 7  MOI = 0.000001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $8.64*10^5$ | $3.59*10^6$ | N.D. | N.D. | N.D. | N.D. |
| Dead cells/ml | $1.3*10^4$ | $3.30*10^4$ | $1.75*10^5$ | N.D. | N.D. | N.D. | N.D. |
| Total cells/ml | $4.35*10^5$ | $8.97*10^5$ | $3.77*10^6$ | N.D. | N.D. | N.D. | N.D. |
| Viability (%) | 97.3 | 96.3 | 95.4 | N.D. | N.D. | N.D. | N.D. |
| Living inf cells/ml | 0 | 0 | 0 | N.D. | N.D. | N.D. | N.D. |
| Dead infected/ml | 0 | 0 | 0 | N.D. | N.D. | N.D. | N.D. |
| Total infected cells/ml | 0 | 0 | 0 | N.D. | N.D. | N.D. | N.D. |
| Infection (%) | 0 | 0 | 0 | N.D. | N.D. | N.D. | N.D. |
| E2 - content (µg/ml) | N.D. | N.D. | 1.0 | 22.7 | 58.6 | 162.1 | 180.8 |

Shake flask No. 8  MOI = 0.00001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $7.38*10^5$ | $2.27*10^6$ | N.D. | N.D. | N.D. | N.D. |
| Dead cells/ml | $1.3*10^4$ | $2.10*10^4$ | $5.00*10^4$ | N.D. | N.D. | N.D. | N.D. |
| Total cells/ml | $4.35*10^5$ | $7.59*10^5$ | $2.32*10^6$ | N.D. | N.D. | N.D. | N.D. |
| Viability (%) | 97.3 | 97.2 | 97.8 | N.D. | N.D. | N.D. | N.D. |
| Living inf cells/ml | 0 | 0 | $1.25*10^5$ | N.D. | N.D. | N.D. | N.D. |
| Dead infected/ml | 0 | 0 | $5.00*10^3$ | N.D. | N.D. | N.D. | N.D. |
| Total infected cells/ml | 0 | 0 | $1.30*10^5$ | N.D. | N.D. | N.D. | N.D. |
| Infection (%) | 0 | 0 | 5.6 | N.D. | N.D. | N.D. | N.D. |
| E2 - content (µg/ml) | N.D. | N.D. | 24.8 | 151.3 | 166.9 | 174.8 | 232.2 |

FIG. 3C

Shake flask No. 9  MOI = 0.0001

| Time | 0 hpi | 23 hpi | 95 hpi | 125 hpi | 144 hpi | 173 hpi | 194 hpi |
|---|---|---|---|---|---|---|---|
| Living cells/ml | $4.23*10^5$ | $7.41*10^5$ | $1.45*10^6$ | N.D. | N.D. | N.D. | N.D. |
| Dead cells/ml | $1.3*10^4$ | $1.50*10^4$ | $1.20*10^5$ | N.D. | N.D. | N.D. | N.D. |
| Total cells/ml | $4.35*10^5$ | $7.56*10^5$ | $1.57*10^6$ | N.D. | N.D. | N.D. | N.D. |
| Viability (%) | 97.3 | 98 | 92.4 | N.D. | N.D. | N.D. | N.D. |
| Living inf cells/ml | 0 | 0 | $1.12*10^6$ | N.D. | N.D. | N.D. | N.D. |
| Dead infected/ml | 0 | 0 | $1.20*10^5$ | N.D. | N.D. | N.D. | N.D. |
| Total infected cells/ml | 0 | 0 | $1.24*10^6$ | N.D. | N.D. | N.D. | N.D. |
| Infection (%) | 0 | 0 | 78.7 | N.D. | N.D. | N.D. | N.D. |
| E2 - content (µg/ml) | N.D. | N.D. | 113.9 | 281.3 | 264.4 | 298.3 | 208.6 |

Relative volumetric E2 protein yield

| MOI | Maximum E2 yield | Average of duplicates | Relative E2 yield |
|---|---|---|---|
| | (µg E2/ml) | (µg E2/ml) | (%) |
| $1*10^{-1}$ (V&S-E2-002) | 57.3 | | |
| $1*10^{-1}$ (V&S-E2-002) | 59.6 | 58.5 | 48.1 |
| $1*10^{-2}$ (V&S-E2-002) | 85.4 | | |
| $1*10^{-2}$ (V&S-E2-002) | 89.8 | 87.6 | 72.1 |
| $1*10^{-3}$ (V&S-E2-002) | 120.6 | | |
| $1*10^{-3}$ (V&S-E2-002) | 122.3 | 121.5 | 100.0 |
| $1*10^{-4}$ (V&S-E2-002) | 169.6 | | |
| $1*10^{-4}$ (V&S-E2-002) | 173.2 | 171.4 | 141.2 |
| $1*10^{-3}$ (V&S-E2-004) | 187.9 | 187.9 | 100.0 |
| $1*10^{-4}$ (V&S-E2-004) | 216.6 | 257.0 | |
| $1*10^{-4}$ (V&S-E2-004) | 298.3 | | 136.7 |
| $1*10^{-5}$ (V&S-E2-004) | 195.7 | | |
| $1*10^{-5}$ (V&S-E2-004) | 232.2 | 214.0 | 113.8 |
| $1*10^{-6}$ (V&S-E2-004) | 144.8 | | |
| $1*10^{-6}$ (V&S-E2-004) | 180.8 | 162.8 | 86.6 |

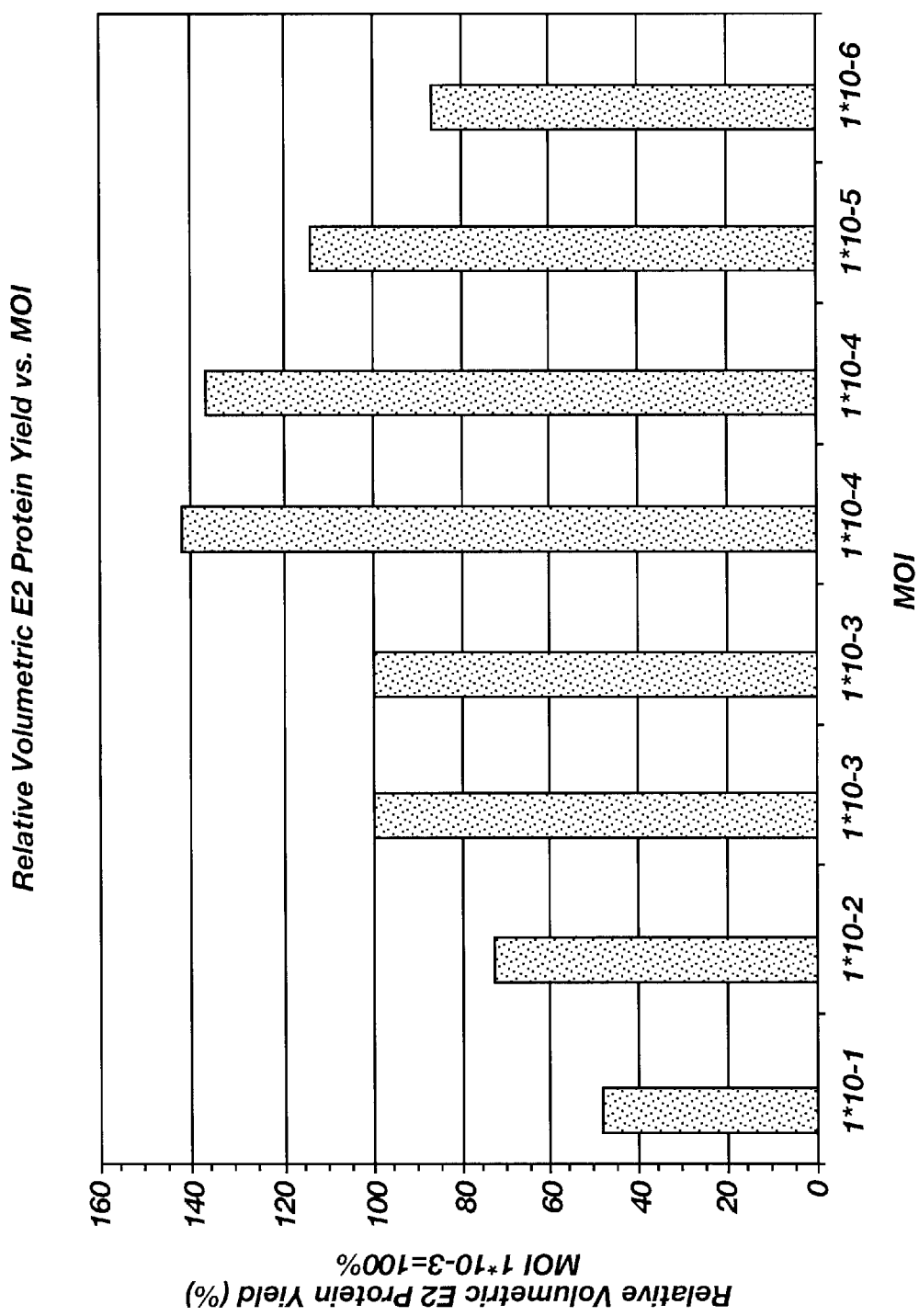

PROTEIN EXPRESSION IN BACULOVIRUS VECTOR EXPRESSION SYSTEMS

CROSS-REFERENCE TO RELATED APPLICATIONS

This application claims continuation status under 35 U.S.C. §§ 120 & 365(c) from co-pending patent application PCT/NL98/00717 filed on Dec. 17, 1998 designating the United States of America, which itself claims priority from European Patent Application EP 97203989.5 filed on Dec. 18, 1997.

TECHNICAL FIELD

The invention relates to methods of increased protein or polypeptide expression in baculovirus vector expression systems. When recombinant-DNA techniques were developed, expectations were high regarding large-scale protein production using genetically modified bacteria. The majority of commercially attractive proteins, however, necessarily undergo post-translational modifications before they can become biologically active proteins. Hence, animal cells are now more frequently used to produce recombinant proteins.

BACKGROUND

Among animal cells, insect cells are of growing importance for the production of recombinant proteins. A convenient and versatile baculovirus vector system using insect cells has been developed. Information on the physiology of insect cells is rather scarce, however, vaccines produced via baculovirus recombinant techniques are generally well accepted. An example is the use of a baculovirus-expressed gp 160 envelope protein of human immunodeficiency virus type I as a possible AIDS vaccine in clinical trials.

Until now, large-scale production of baculovirus-expressed proteins in insect cells was limited to bioreactors of up to about 10 liters. Scale-up suspension cultures offer the best possibility. In large-scale production (see Tramper et al., Rec. Adv. Biotech., 1992, 263–284; Power and Nielsen, Cytotechnology 20: 209–219, 1996), special emphasis should be given to factors influencing cell growth and virus production. Variations in such factors greatly influence the final level of recombinant protein production.

Baculoviruses are characterized by rod-shaped virus particles which are generally occluded in occlusion bodies (also called polyhedra). The family Baculoviridae can be divided in two subfamilies: the Eubaculovirinae comprising two genera of occluded viruses—nuclear polyhedrosis virus (NPV) and granulosis virus (GV)—and the subfamily Nudobaculovirinae comprising the nonoccluded viruses. The cell and molecular biology of *Autographa californica* (Ac)NPV has been studied more in detail.

Many proteins have been expressed in insect cells infected with a recombinant baculovirus encoding that protein. Encoding means that such viruses are provided with a nucleic acid sequence encoding a heterologous protein and often are further provided with regulating nucleic acid sequences, such as a promoter. Most often, the polyhedrin promoter is used to express a foreign gene but the p10 promoter is equally well suited and used as well.

Several cell-lines are available for infection with recombinant baculovirus. The cell-line SF-21 was derived from ovarial tissue of the fall armyworm (*Spodopterafrugiperda*), A clonal isolate, SF-9, available from the American Type Culture Collection (CRL 1711), is more or less a standard cell-line for in vitro production of recombinant virus and is said to be superior in producing recombinant virus. Other cell-lines are, for example, the Hi-Five cell-line and the Tn-368 and Tn-368A cell-lines obtained from the cabbage looper (*Trichoplusia ni*). The most widely used media in which insect cells grow include TNM-FH, BML-TC/10, and IPL-41. These media are usually supplemented with more or less defined components, such as mammalian sera, in particular, fetal calf serum. Serum replacements have also been applied to insect-cell culture, and serum-free media, such as Ex-cell 400™ and Sf900 are commercially available.

Insect cells, in general, grow on solid supports as well as in suspension, but are reported to give higher yields of virus when grown on solid supports. Infection is most efficient when cells are infected in the exponential growth phase. The amount of polyhedra and virus produced per cell, however, does not vary significantly between cells infected during different stages in the cell cycle. Cell density has a great influence on virus production. Insect cells can show a form of contact inhibition resulting in reduced virus production at higher cell densities.

The initial multiplicity of infection ("m.o.i." or "MOI"), which is the number of infectious viruses per cell, generally influences both the fraction of infected cells and the number of polyhedra per cell at the end of infection. Optimal m.o.i. for virus production is generally considered to be at around 20–30. In a study (Licari and Bailey, Biotech. Bioeng., 37:238–246, 1991) of a recombinant baculovirus expressing β-galactosidase, Sf-9 cells were infected with m.o.i. values between 0 and 100. The β-galactosidase yield increased and cell density decreased with increasing m.o.i. It is generally thought that increasing or decreasing m.o.i. has only a limited affect on the maximum achievable yield of a recombinant protein per infected cell. Choosing low m.o.i., however, allows reduction of virus stock needed for infection and minimizes the risk of the generation of defective interfering particles of baculovirus. If a batch culture of insect cells is infected at high m.o.i. (>5), the ensuing infection process will be essentially synchronous, i.e., all cells will go through the infection cycle simultaneously. When cells are infected at an m.o.i. <5 in a batch culture, the culture will no longer be synchronous. The culture will initially be composed of noninfected cells and cells at different points in their individual infection cycle until all cells have been infected and the production of wanted protein comes to an end. In general, in such cultures the production levels are much lower. The culture behavior is the combined behavior of the individual cells that are each in a different phase of production, thus, the suboptimal production levels. In a continuous culture, noninfected cells are added continuously and the culture will obviously be asynchronously infected.

Through designing mathematical models, it is thought possible to predict complex behaviors such as those observed when infecting cells at low m.o.i. or when propagating virus in a continuous culture system. A purely empirical analysis of the same phenomena is considered very difficult, if not impossible. At present, three models are known: the Licari & Bailey, the de Gooijer and the Power & Nielsen model. These are, despite their complexity and the effort that has gone into developing them, all first generation models, postulating about the behavior of baculoviruses expressing a model recombinant protein (β-galactosidase) expressed under control of the polyhedrin promoter. They summarize, to a large extent, our present quantitative understanding of the interaction between baculovirus and insect cells, when looked upon as a black box system, with disregard to DNA and RNA accumulation and the infection cycle. The binding and initial infection processes are still quantitatively poorly understood and further work in this area is much needed.

The baculovirus expression system offers a powerful tool for recombinant protein production. Several cell-culture configurations can be used for large-scale production. These systems, however, need further optimization to take full advantage of their potential. For commercial application, large-scale and low-cost production is pivotal. Polyhedra-production systems reported in large-scale cell cultures should be dramatically improved to meet the commercial demands for a price-competitive product.

SUMMARY OF THE INVENTION

The invention provides a method for large-scale recombinant protein production using the baculovirus expression system allowing increased or improved yields of the wanted protein. The invention provides a method to produce and improve yield of a recombinant protein in insect-cell culture which comprises selecting a recombinant baculovirus encoding said protein, growing insect cells in growth medium in a culture vessel, and infecting the cells with a multiplicity of infection of <0.01.

In a preferred embodiment, the invention provides a method to increase yield of a recombinant protein produced in insect-cell culture which comprises selecting a recombinant baculovirus encoding said protein, growing insect cells in growth medium in a culture vessel and infecting the cells with an inoculum of at least one baculovirus with a multiplicity of infection of <0.01. Increasing yield has been a topic of several research groups. For example, Chen et al. (Drug metabolism and Disposition: 24 399–405, 1997), studied the possibility of optimizing the MOI for a co-infection approach, whereby two different baculovirus-expressed proteins were produced in insect cell culture. Contrary to the results described herein, they found for their two proteins a best MOI of approximately 0.015 to 0.03. Reducing the MOI to <0.01 reduced the yield of the co-infection system of Chen et al. Radford et al. (Cytotechnology 24, 73–81, 1997), not being hindered by studying a co-infection system, clearly indicate that MOI's >1 should always be used to maximize final process yields, again teaching against the findings of the present invention. They state that it is impossible to produce larger amounts of protein and virus per cell using low MOI and suggest adjusting the time of infection (TOI) instead.

Others, such as Nguyen et al. ( J.Biotech. 31, 205–217, 1993), do not find a solution in changing MOI, but aim at increasing yields by applying fed-batch cultures, or change the temperature under which the virus is grown (Wu et al., Cytotechnol. 9, 141–147, 1992; King et al., Biotechnol. Bioeng, 38, 1091–1099, 1991) and avoid growing the virus under MOI <0.01.

These earlier results clearly differ from those provided in this description (see, for example, FIG. 1), where cultures infected with an MOI <0.01 (such as 0.003, 0.001, or even 0.0001) reached higher yields than those infected with MOI 0.01 or 0.1.

A preferred embodiment of the invention provides a method to produce and improve yield of a recombinant protein in insect-cell cultures not grown in monolayer cultures. Conventional laboratory methods to produce proteins in the baculovirus expression vector system in small amounts use monolayer cultures of insect cells in culture flasks. These static cultures are normally infected with a high MOI, to ensure synchronous infection. It is pivotal that all cells are infected before the monolayer has become confluent, since contact inhibition will lead to metabolic changes in the cells which may affect the final product yield. Since it is difficult to accurately establish the cell density in monolayer cultures, it is impossible to carry out MOI experiments. It is even more useless to use a low MOI (<0.01) to infect the cultures. Both over- and under-estimation of the cell density at the time of infection will lead to a significantly suboptimal protein yield.

Routinely, one uses a high MOI, which guarantees a synchronous infection of the total cell population. This implies that large virus stocks are needed to infect the monolayer culture to achieve optimal yields.

Scale-up of protein production using monolayer cultures simply means using more tissue culture flasks. The production of large amounts of protein using monolayer cultures is very labor-intensive. Furthermore, it is not possible to regulate and/or monitor important culture parameters such as dissolved oxygen concentration and pH.

The invention now provides a method suitable for all insect cell cultures and the insight that a low MOI is beneficial for optimizing yield in insect cultures other than monolayer cultures.

Different types of culture vessels can be used for culturing insect cells other than in monolayer cultures. The aim of every fermentor design is achieving sufficient aeration and high cell density, while keeping the shear forces as low as possible (Tramper et al. in "Recent advantages in biotechnology," eds. Vardar-Sukan and Sukan, 1992). In the majority of the cases described in the literature, a stirred tank bioreactor equipped with a gas sparger is used. In this type of vessel, homogeneity is achieved by using an impeller. This type of fermentor can be operated in different methods. First of all is the batch method. This is the most straightforward and simple method. Cells are cultured, virus is added and the product is harvested at the end of the infection. A more complicated method is fed-batch culture. A concentrated mixture of nutrients is added to the culture vessel to achieve higher cell densities and higher volumetric product yields (Nguyen et al. 1993 Journal of Biotechnology vol. 31, p.205–217). This is more complicated since it is not always clear what the limiting nutrient is. Canceling one nutrient limitation by adding this substrate may directly lead to another substrate limitation and, thus, not necessarily to higher product yields.

A different method of mixing is used in airlift bioreactors (Wu et al. 1992 Cytotechnology vol. 9 p. 141–147). This type of vessel consists of two cylinders. The cylinder with the smallest diameter (draft tube) is placed inside the cylinder with the bigger diameter (downcommer). In the center cylinder air or another gas is sparged, creating an upward flow. At the top of the fermentor the gas leaves the fluid and the fluid goes down outside the center cylinder.

In this way, both aeration and homogeneity are achieved using sparging of gas only, due to the difference in density in the draft tube and the downcommer. This method may reduce shear stress. However, continuous aeration rates are needed to achieve proper mixing.

Another method to raise the living cell density in a fermentor is by including a spin filter or another cell-retaining device. This is called perfusion. This allows removal of waste medium from the fermentor and addition of fresh medium, while retaining the cells in the fermentor. This method results in a lot of extra equipment and more difficult fermentor operation (Caron et al. 1994 Biotechnology and Bioengineering vol. 43, p. 881–891). Furthermore, methods such as a macroporous-bed and immobilization in a gel-matrix are reported. These types of methods rely on immobilization of the cells on or inside a matrix, making it possible to remove waste medium and add fresh medium without diluting the cell culture. If cell densities, contact inhibition and other related problems of monolayer cultures would be manageable, a method according to the invention could not only be applied in the above discussed various culture systems but in monolayer cultures as well.

For example, a preferred embodiment of the invention provides a method to produce and improve yield of a recombinant protein in insect cell cultures which comprises selecting a recombinant baculovirus encoding said protein, growing the insect cells in growth medium in a culture vessel with a sufficient volume to contain at least 2 liters, and infecting the insect cells with an inoculum of at least one baculovirus with an m.o.i. of <0.01 PFU of said baculovirus/cell. The invention provides a method wherein multiplicities of infection are used that are considerably lower than, for example, the m.o.i. of 1–5 leading to an asynchronously infected culture. By infecting insect cultures with a baculovirus using an m.o.i. as provided by the invention, an optimal balance is achieved between the speed of replication of the cells in relation to the speed of replication of the virus, thereby allowing optimal expression of the wanted protein. A method provided by the invention can be easily adjusted to higher or lower cell densities by adjusting the m.o.i. as well, wherein the relative ratio of virus particles available for infecting the cells in the various phases of replication remains according to the multiplicities and densities provided by the invention. A preferred embodiment of the method according to the invention comprises growing the cells in a culture vessel with a sufficient volume to contain at least 10, more preferably at least 20, and most preferably at least 50 to 250 liters growth medium, thereby allowing scaling-up of baculovirus cultures expressing heterologous proteins. One can use a culture vessel with a volume that is larger than needed for the volume of growth medium that is present, e.g., one can use 100 L culture vessels to cultivate 20–70 liters cell-culture. A preferred embodiment of the method according to the invention comprises infecting the cells at a cell density of $1 \times 10^5$ to $5 \times 10^6$ cells/ml, more preferably at $5 \times 10^5$ to $1,5 \times 10^6$ cells/ml, thereby keeping the actual volume of the virus inoculum within easily manageable limits. Yet another embodiment of the method according to the invention comprises infecting the cells with an m.o.i. $\leq 0.005$, such as 0.003, 0.001, 0.0005 or 0.00025, whereby the inoculum is kept as small as possible. A preferred embodiment of the method according to the invention comprises selecting a recombinant baculovirus expressing the wanted protein under control of the p10 promoter. The p10 promoter is playing a role in cell lysis. Absence of the p10 protein causes the infected cells to remain intact and prevents the release of polyhedra from infected cells, thereby reducing reinfection rates but not infectivity, per se. The whole process of virus infection can now be checked visually, due to the fact that the polyhedrin gene, and thus the polyhedra, are still present. Virus infection can be observed as dense protein particles that accumulate in the cell nucleus. Another embodiment of the method according to the invention comprises growing the insect cells in a batch culture system, thereby minimizing the accumulation of defective interfering baculovirus particles which can compromise infection and replication of yet uninfected cells. Another embodiment of the method provided by the invention comprises growing the insect cells in suspension, preferably in a culture vessel such as a fermentor, which can be moderately stirred. The use of stirred suspension cultures, especially when combined with using a recombinant baculovirus wherein the wanted protein is under control of the p10 promoter to visually check virus growth (but other methods of checking, e.g., in the case of using the polyhedrin promoter, such as observing CPE, are also available) allows for a better control of the culture.

Moderate stirring of the suspension guarantees a homogenous culture in which no substrate gradients are built up and in which the cells are not subjected to too high shear forces.

Furthermore, stirring results in an efficient transfer of viruses from infected to noninfected cells, giving a higher efficiency of virus infection of cells. Since initially only about 0.1–0.3% of the cells is infected, the remaining 99.7–99.9% of cells are allowed to grow and multiply.

The invention provides a method to express and produce recombinant protein of various origin. An example provided by the invention is the production of pestivirus-derived protein to a concentration of said protein in the growth medium at harvest of at least 100, 120 or 150 µg/ml, and more preferably at least 200 or even 300 µg/ml. The wanted protein can also be used to prepare antigenic substances for veterinary or medical use, e.g., incorporated in a vaccine or in a diagnostic test. The wanted protein produced by a method according to the invention can, for example, be used to prepare a vaccine.

An example provided by the invention is the pestivirus E2 protein or fragments thereof, which can, for example, be used to prepare a vaccine against pestivirus infections, such as classical swine fever in pigs. In a preferred embodiment, the invention provides a vaccine comprising recombinant pestivirus E2 or $E^{rns}$ protein or fragments thereof characterized in that it is not being immunoaffinity purified and preferably confers protection against a pestivirus infection at the PD95 level after one single vaccination with one dose. This is particularly relevant for CSFV vaccination. When applied, CSFV vaccination generally is performed during a mass campaign in an area where an outbreak of CSFV has occurred. This calls for rapid vaccination of large numbers of animals in a relatively short period. In such a mass campaign it is of imminent importance that an adequate protection level (the number of pigs that are protected against the wild-type virus infection) is achieved rapidly. Waiting for several weeks after a first vaccination for a second vaccination in order to achieve protection greatly hampers and delays the control of the disease. Differences between various methods to produce the recombinantly expressed E2 protein, even when comparing E2 fragments expressed in baculovirus, exist. In earlier reported E2 protein production cultures, the E2 protein fragment yield varied between 20–90 µg/ml (Hulst et al., J. Virol. 5435–5442, 1993; Hulst and Moormann, Cytotechnology 20:271–279, 1996), further necessitating immunoaffinity-purification with monoclonal antibodies to obtain the necessary and relevant E2 antigenic mass for single shot vaccination. Another method (using a fragment of E2 described in EP 0389034) which uses E2 harvested from the supernatant of insect cells without further immunoaffinity purification, results in an E2-based vaccine that is injected twice before a satisfying (protective) immune response is obtained. Although a vaccine (Porcilis®Pesti) comprising E2 antigen is currently registered, this vaccine needs to be applied twice, thereby seriously hampering the usefulness of vaccinating against classical swine fever infections with this vaccine since it takes at least two vaccinations with a 4-week interval to provide the wanted immune response.

These problems (which are solved by the present invention), among others, relate to a low concentration of the relevant antigenic substance, in this case the E2 protein fragments in the starting material, e.g., the cell culture supernatant, from which the vaccine is prepared. In theory, one can further accumulate antigenic mass by purification and condensation methods known in the art. However, this does not lead to a commercially attractive vaccine production because of high costs per dose. Another example is the pestivirus $E^{ms}$ protein, which can also be used in a vaccine, in diagnostic tests or in other therapeutic substances.

For example, Ruggli et al. (Virus Genes 10:115–126, 1995) grows a baculovirus expressing E2 in monolayer insect cell culture to a maximum yield of no more than 5–10 $\mu g/10^6$ cells. Furthermore, Moser et al. (Vet. Microbiol. 51:41–53), grows the E2 of Ruggli et al., in monolayer insect cell culture using an MOI of 5 and cannot produce enough antigen in unconcentrated form for ELISA purposes. In their experience, further purification by nickel-chelate affinity chromatography of the protein is a prerequisite to simplify handling and improve ELISA quality. No vaccine preparation was contemplated with the thus prepared E2 protein.

When vaccination was the aim of the research, it was found that vaccination needed to occur twice, using an immunopurified E2 protein, to achieve a certain measure of protection. For example, in Hulst et al. (J. Virol. 67:5435–5442, 1993), WC 95/35380, and van Rijn et al. (J. Gen. Virol. 77:2737–2745, 1996), E2 was produced in monolayers and immunoaffinity purified to achieve a protective vaccine.

An example provided by the invention is a vaccine comprising recombinant CSFV E2 protein fragments which, now that sufficient large amounts can be produced, no longer need to be immunoaffinity purified before it is incorporated in a vaccine that confers protection (at a protective dose level of 95% (PD95)) against a classical swine fever virus infection within two to three weeks after the animals received one single vaccination with one dose. A method provided by the invention provides a vaccine comprising recombinant pestivirus E2 or $E^{ms}$ protein, or fragments thereof, that confers protection against a pestivirus infection after one single vaccination with one dose, while the protein fragment has not been purified by immunoaffinity. The invention also provides a vaccine comprising a protein provided by the invention which additionally comprises an adjuvant. Suitable adjuvants are known to the average person skilled in the art, e.g., Freund adjuvants, or aluminum hydroxide, or emulsions, such as water-in-oil, double water-in-oil, or oil-in-water emulsions. The desired protein can also be used to prepare other substances for veterinary or medical use. Yet another example provided by the invention is a hormone-like substance, such as the follicle stimulating hormone FSH ($\alpha$-units and/or $\beta$-units and complexes and fragments thereof), which can be produced by infecting an insect cell culture with one baculovirus expressing the $\alpha$-unit and/or with another baculovirus expressing the $\beta$-unit in the culture. A method according to the invention can also be used for large-scale and low-cost production of recombinant baculoviruses as bioinsecticides. A preferred embodiment is the use of recombinant viruses utilizing the p10 promoter for foreign gene expression in the production of bioinsecticides since insects generally get less infected by baculovirus lacking the polyhedra gene. Culturing other recombinant baculoviruses expressing other recombinant proteins with a method according to the invention and production and/or use of such virus proteins for incorporation in insecticidal, medical, therapeutic, and/or antigenic substances or products is within the skills of the artisan. The invention is further illustrated in the following experiments but is not limited thereto.

BRIEF DESCRIPTION OF THE DRAWINGS

FIG. 1 consists of two tables illustrating the data of E2 stability in prolonged culture experiments;

FIGS. 3A–3C are tables illustrating data from various MOI experiments; and

FIGS. 4A–4G are graphs depicting data from various MOI experiments.

DETAILED DESCRIPTION OF THE INVENTION

Experiments

Figure 2A:
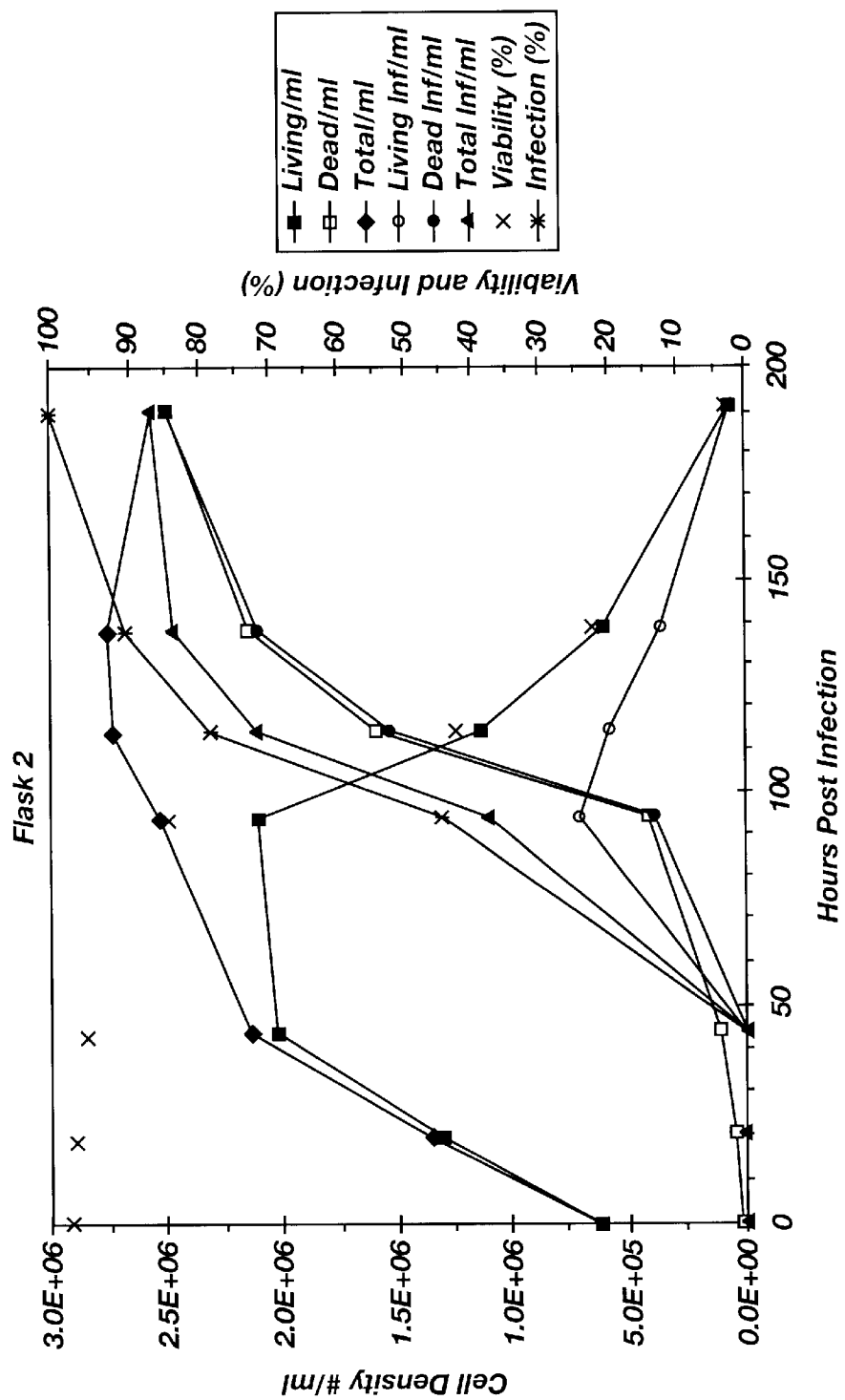
FIGS. 2A–2C are graphs illustrating the stability of E2 in culture experiments.
Figure 2B:
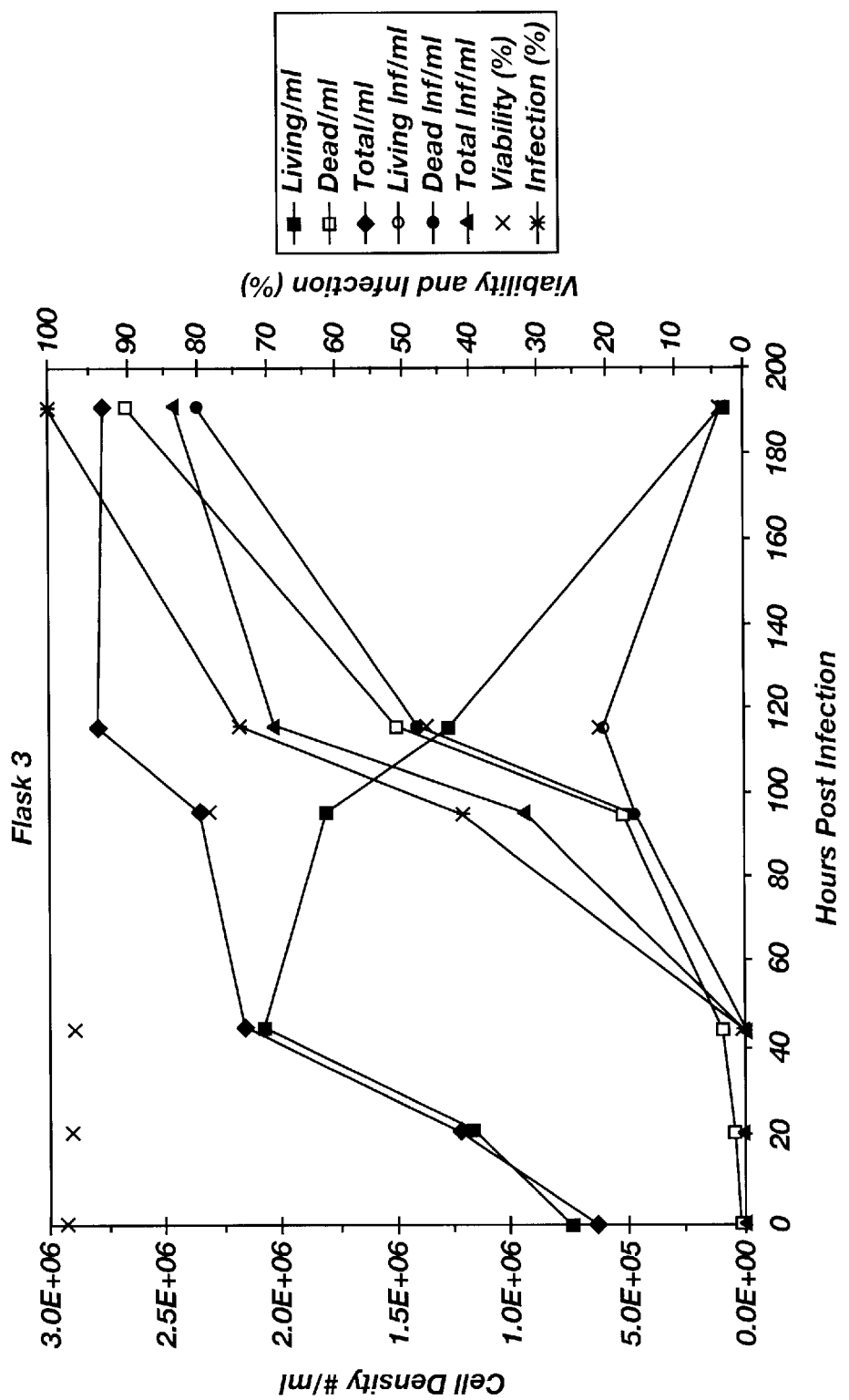
Figure 2C:
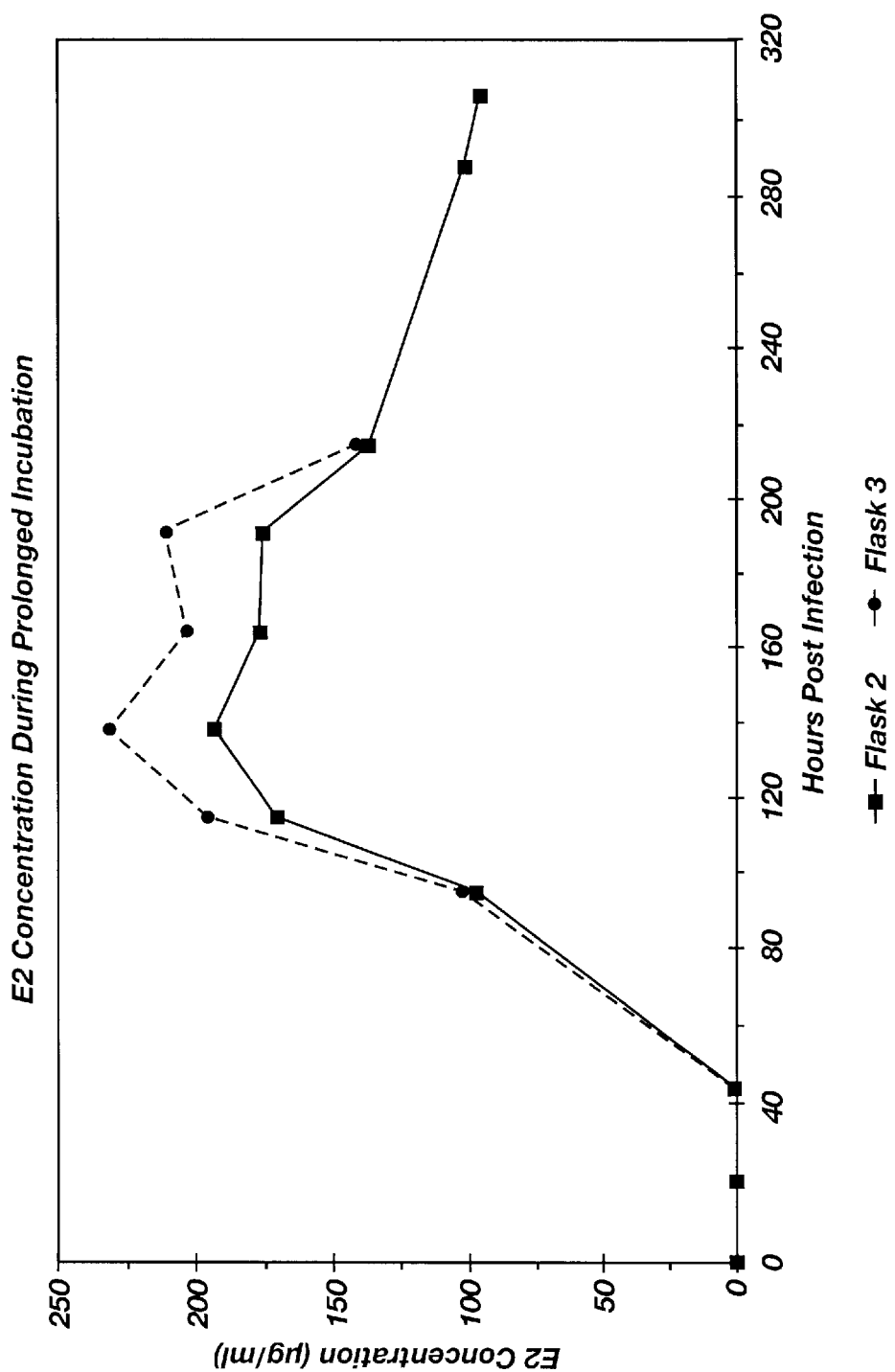
Figure 4A:
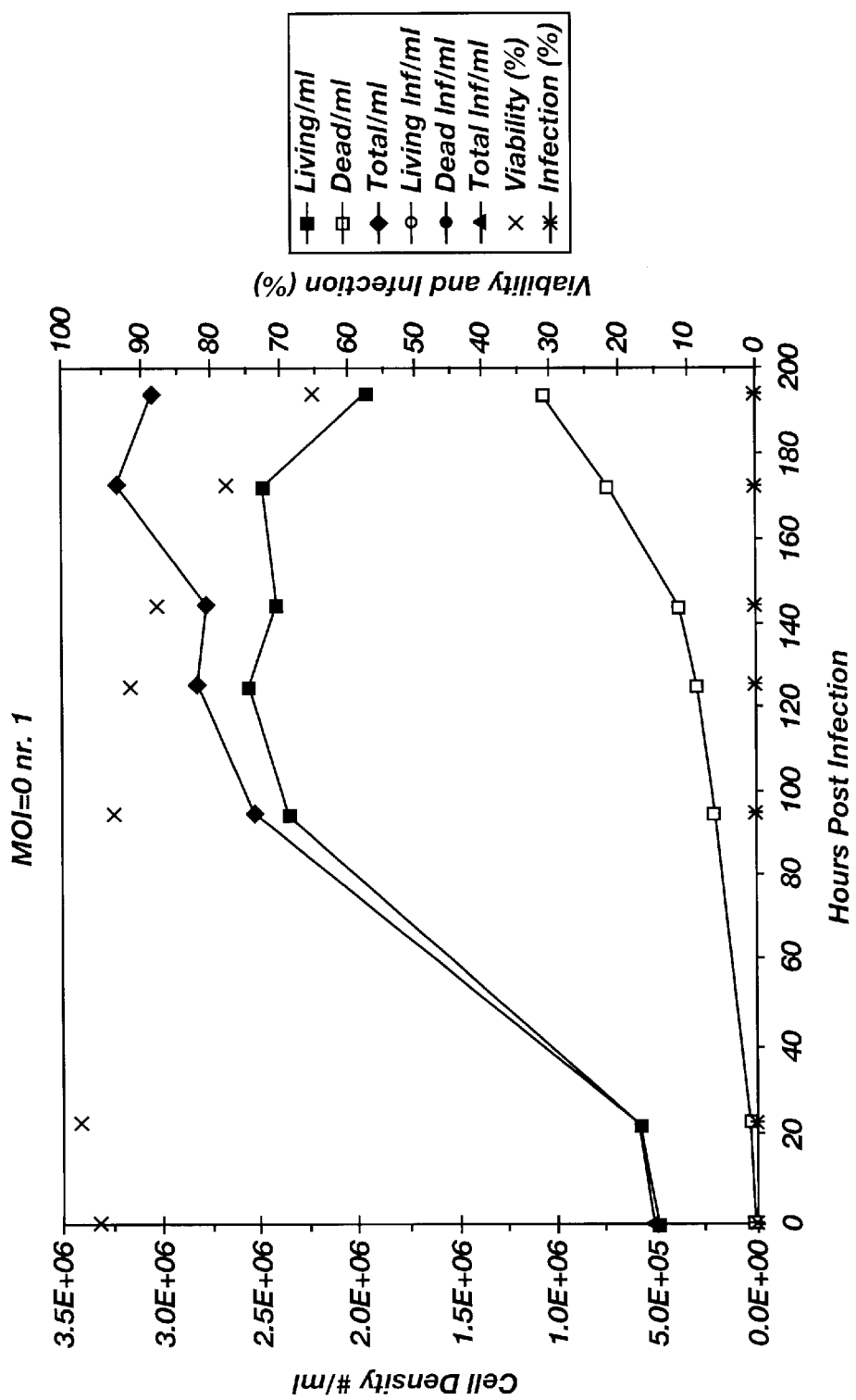
Figure 4B:
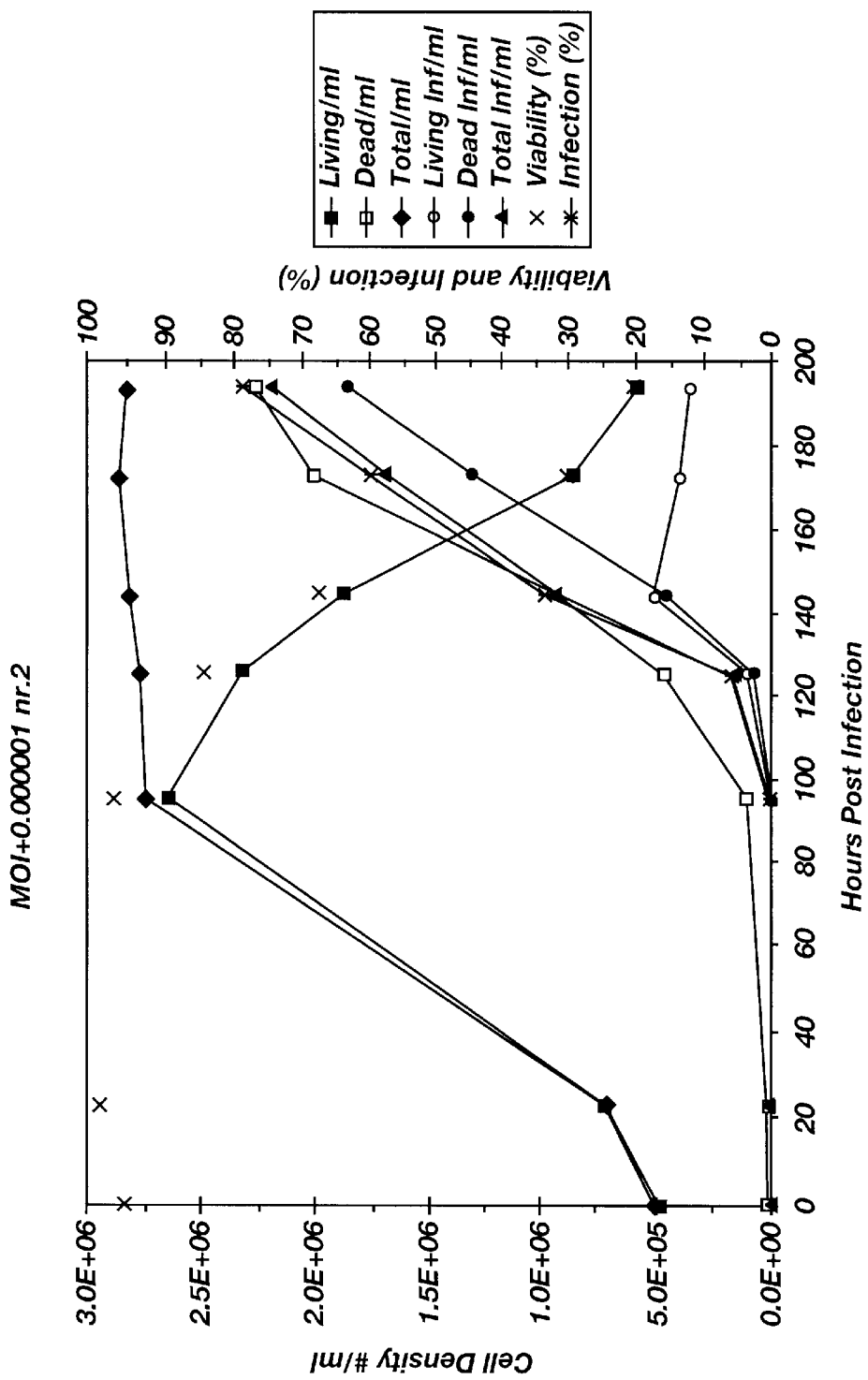
Figure 4C:
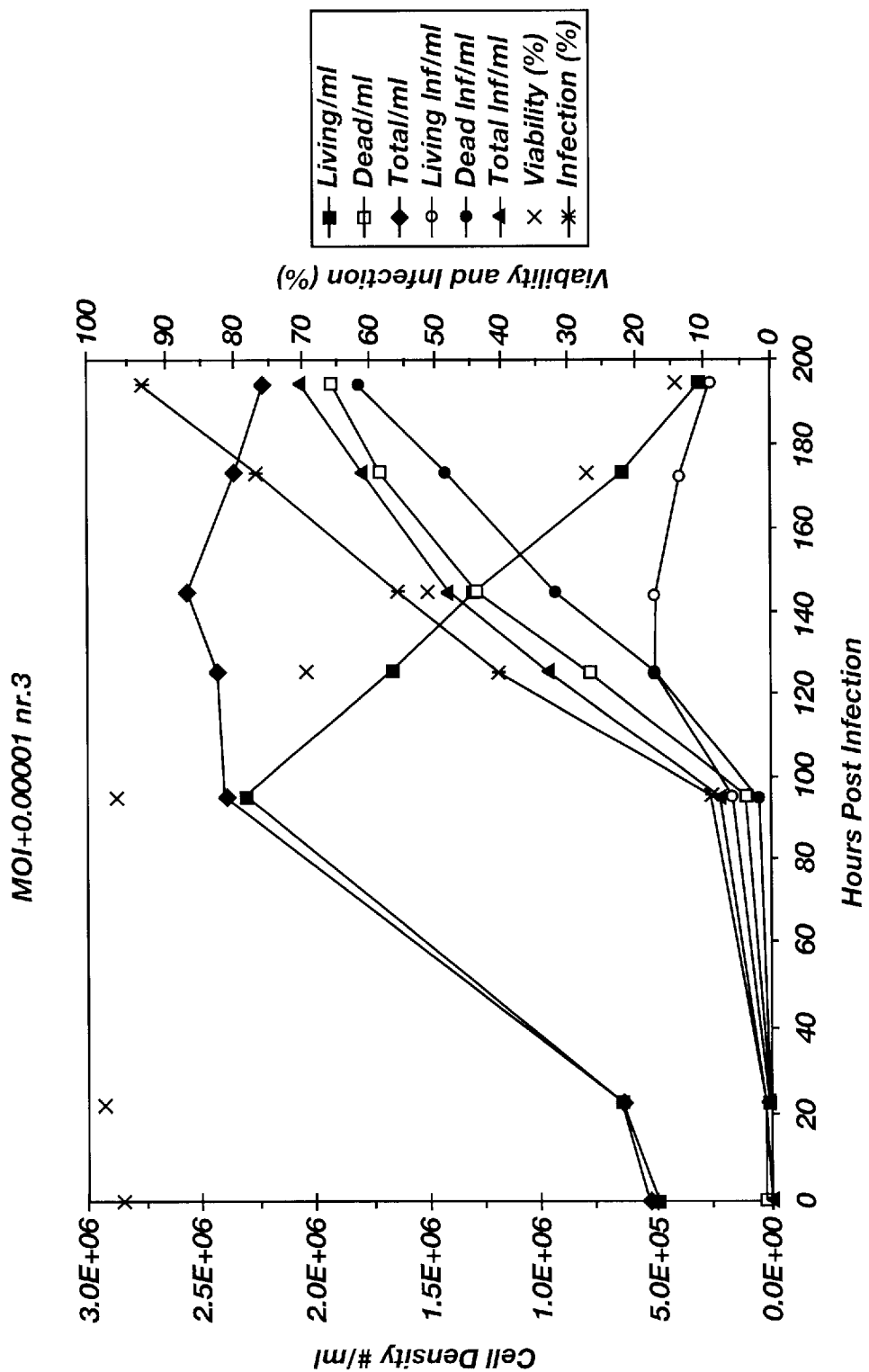
Figure 4D:
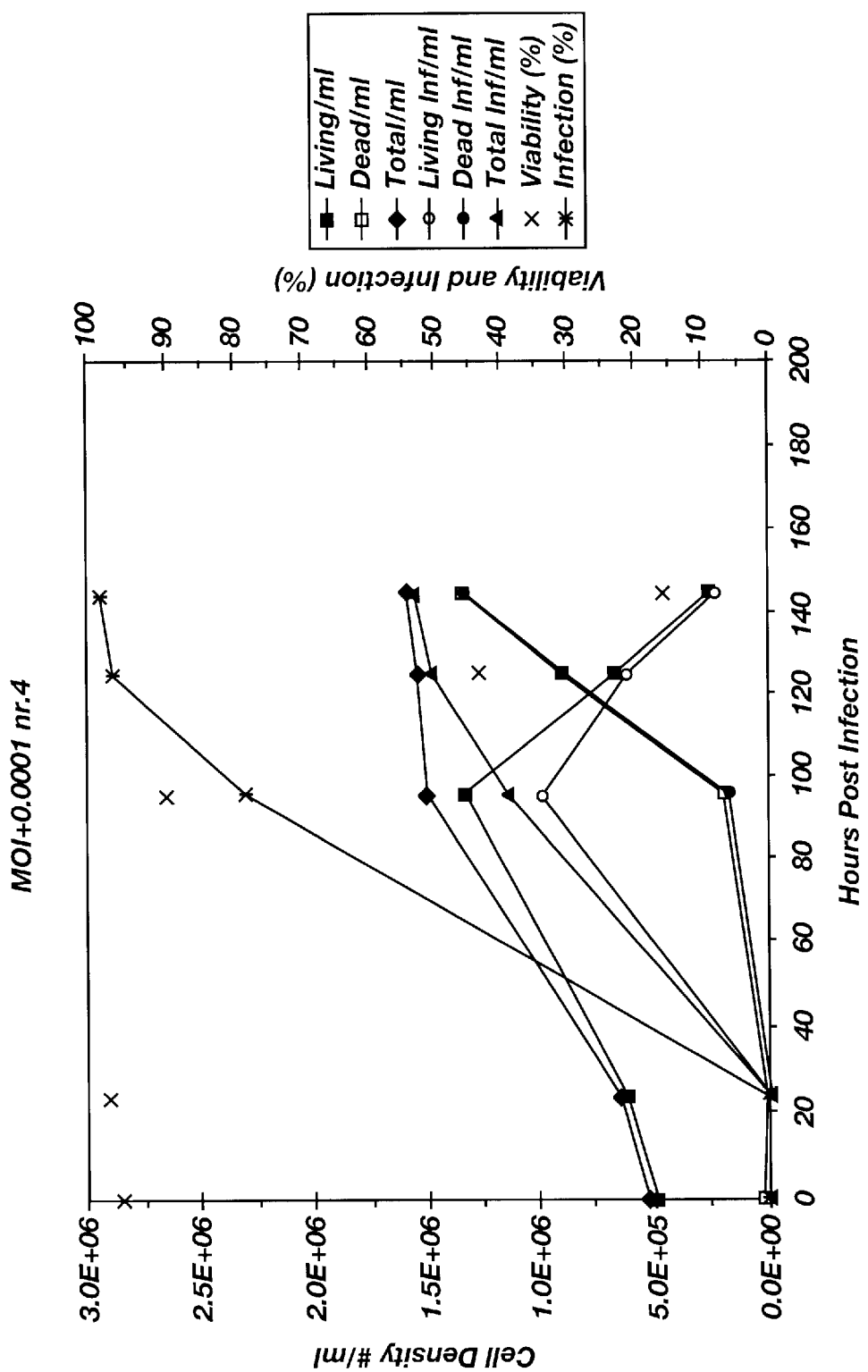
Figure 4E:
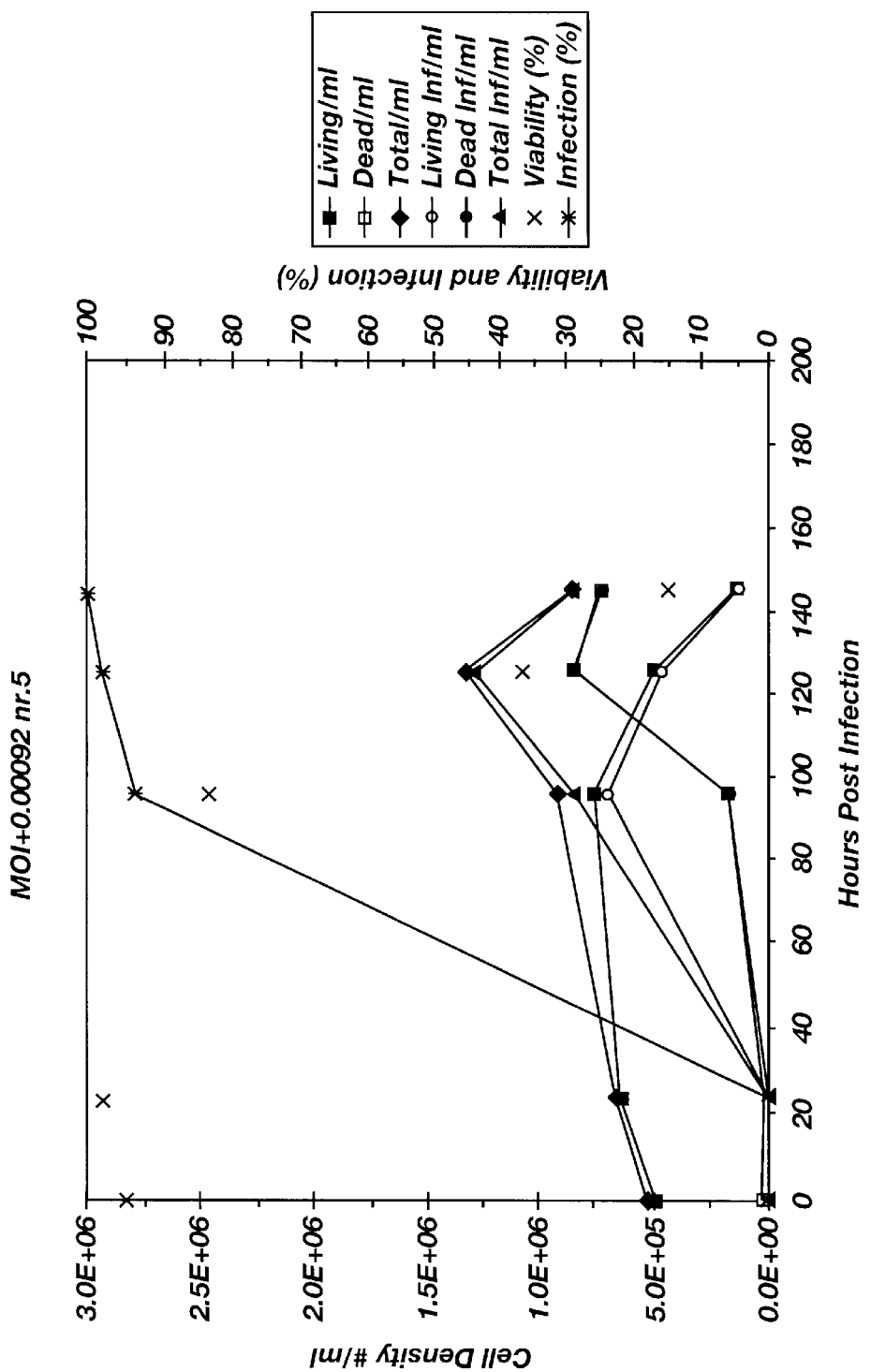
Figure 4F:
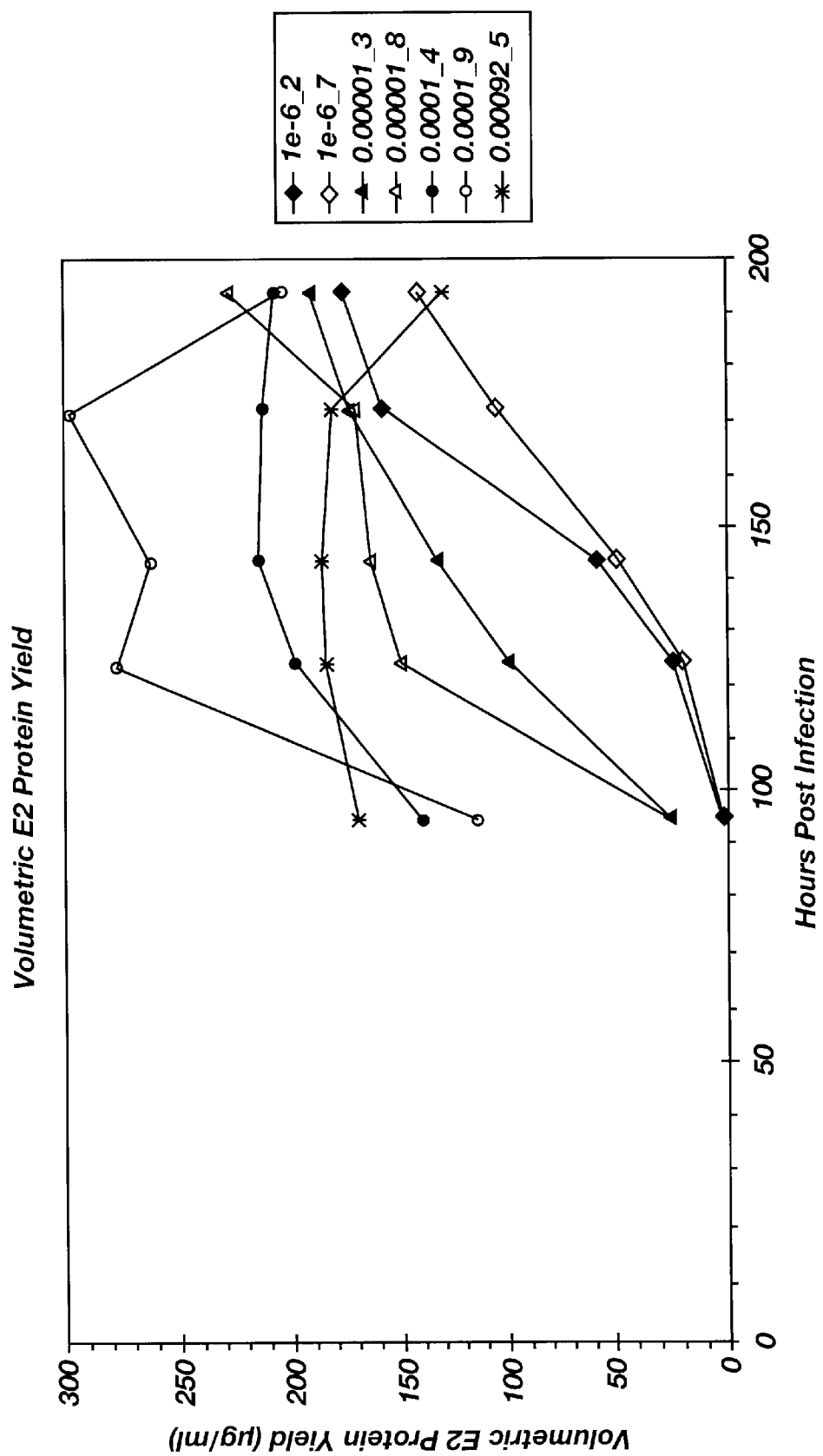

The genus Pestivirus of the family Flaviviridae conventionally consists of classical swine fever virus (CSFV), border disease virus (BDV), and bovine viral diarrhea virus (BVDV). Genomes of several BVDV and CSFV strains have been sequenced (Renard et al., 1987 EP application 0208672; Collett et al., 1988, Virology 165, 191–199; Deng and Brock, 1992, Virology 1991, 865–679; Meyers et al., 1989, Virology 171, 555–567; Moormann et al., 1990, Virology 177, 184–188). For BDV, only incomplete genomic nucleotide sequences are yet available. The pestivirus genome is a positive-stranded RNA molecule of about 12.5 kilobases containing one large open reading frame. The open reading frame is translated into a hypothetical polyprotein of approximately 4,000 amino acids, which is processed by virus—and cell-encoded proteases. The open reading frame is flanked by two highly conserved small nontranslated regions, which are probably involved in the replication of the genome. The 5'-noncoding region also plays a role in initiation of translation.

The polyprotein, which is co—and post-translationally processed by cellular and viral proteases, contains all the viral structural and nonstructural proteins (for review, see C. M. Rice: In Fields Virology, Third Edition, 1996 *Flaviviridae*: The Viruses and their Replication, Chapter 30, pp. 931–959). The viral structural proteins, among which are the envelope proteins $E^{ms}$, E1 and E2, are located in the N-terminal part of the polyprotein. The nonstructural proteins, among which are the serine protease NS3 and RNA replicase complex NS5A and NS5B, are located in the C-terminal part of the polyprotein.

Animals infected with a pestivirus develop antibodies against $E^{ms}$, E2 and NS3. However, only antibodies directed against E2 are strongly virus neutralizing, whereas those directed against $E^{ms}$ and NS3 have only a low virus neutralizing capacity, or none at all. This knowledge prompted us to start evaluation of the suitability of E2 as a CSFV subunit marker vaccine. In this setup, $E^{ms}$ and/or NS3 could be used for development of the diagnostic test accompanying the E2 marker vaccine.

To date, BDV and BVDV have been isolated from different species, whereas CSFV seems to be restricted to swine. Pestiviruses are structurally and antigenically closely related. Envelope glycoprotein E2 is the most immunogenic and most variable protein of pestiviruses. We cloned E2 genes of many different pestivirus strains, including those from a deer and a giraffe. The E2 genes were transiently expressed, characterized with monoclonal antibodies, sequenced and compared. P. A. van Rijn et al., 1997, Virology, 237: 337–348. Based on this data, we can delineate six major groups within the pestivirus genus. Four groups correspond to defined genotypes, whereas the other two groups are new genotypes within the pestivirus genus. One group comprises CSFV strains isolated from swine. A second group consists of BDV strains Moredun, L83 and X818, which have been isolated from sheep, and strain F from swine. A third group contains strain BD78 from sheep, strain 5250 from swine and strain 178003 from cattle. On the basis of E2, these viruses are very similar to BVDV strains associated with acute severe outbreaks of bovine viral diarrhea, so called type 2 BVDV. The fourth group consists of BVDV strains predominantly originating from cattle. This BVDV group can be divided into two subtypes or subgroups, BVDV-1a and 1b. BVDV-1a contains viruses from the USA, like NADL and Oregon, and some others, like 150022 and 1138, from Europe. Subgroup BVDV-1b contains strain Osloss and several Dutch isolates. The fifth and sixth "groups" could be proposed as two new genotypes and contain strains Deer and Giraffe, respectively.

The development of marker vaccines for veterinary use has led to new concepts for control and eradication of economically important viral diseases of livestock. The use of a marker vaccine allows serological discrimination between vaccinated and field virus-infected animals, and thereby a controlled elimination of the virus. For instance, in most member states of the EU, vaccination against Aujeszky's disease (AD) is allowed with gE-negative vaccines only. Animals infected with an AD field virus do develop antibodies against gE. An ELISA test which detects these antibodies is used for the detection of infected animals, which subsequently may be removed from a herd, and for monitoring the status of field virus infections in a herd during prolonged vaccination campaigns. Eventually, the aim is to reach a field virus free status of a herd. Vaccination can then be discontinued and a serological surveillance program to guard this status should come into force. Thus, vaccination with a marker vaccine will reduce the costs of eradication campaigns which rely on stamping out of infected herds, instead of only the infected individual animal. If performed on a large enough scale and during a long enough period, this may even be a faster method to reach the field virus free status of the pig population than stamping out the infections.

Now and in the future, when current endemic diseases like AD have been eradicated, there is still use for marker vaccines, e.g., to control outbreaks of diseases which have been eradicated from the population and against which there is no routine vaccination anymore. In such cases where an animal population is serologically naive, highly contagious diseases may spread explosively and can then cause enormous economic losses.

Many examples have shown that the baculovirus system supports high-level expression of heterologous proteins. High-level expression is highly advantageous because dead subunit vaccines are generally only capable of eliciting a protective immune response when a large amount of antigen is applied. In our first approach, two recombinant baculoviruses, one expressing E2 with a TMR (BacE2[+]) and the other expressing E2 without a TMR (BacE2[-]), were constructed (Hulst et al., 1993, J. Virol. 67:5435–5442). Note that in this publication and other comparable publications, E2 is still designated with, its old name E1. E2 without a TMR was secreted into the cell culture medium whereas E2 with a TMR was not. Furthermore, both E2s reacted identically with monoclonal antibodies representing each of the four antigenic domains on E2. This suggested that the antigenic properties of cell-associated and secreted E2 were identical, and because secreted E2 was produced to much higher levels than cell-associated E2 (ten-fold higher), it was decided to test secreted immunoaffinity purified E2 in a vaccination trial in pigs. Two vaccine formulations containing 20 μg E2/ml and 100 μg E2/ml in a double water-oil adjuvant were prepared. Of four groups of 2 SPF pigs, two were vaccinated IM with 20 μg E2, and two with 100 μg E2. After 28 days, I group vaccinated with 20 μg E2 and 1 group vaccinated with 100μg E2, were revaccinated with the same dose E2. At day 42 all animals were challenged intranasally with virulent CSFV strain Brescia. Regardless of the vaccine dose applied, all vaccinated pigs had mounted neutralizing antibodies at day 28, though to different levels. Up until day 42, the day of challenge, antibody titers kept rising to high levels in all animals, whether they were boosted or not. Therefore, it was not surprising that even animals which were vaccinated only once with a dose of 20 μg immunoaffinity purified E2, were already completely protected against CSF (Hulst et al., 1993 J. Virol. 67:5435–5442).

Because animals infected with pestiviruses invariably develop antibodies against $E^{ms}$ (Kwang et al., 1992, Vet-.Microbiol. 32: 281–292), a second viral envelope glycoprotein, one of the viral proteins most suitable for diagnostic test development in conjunction with E2, was used. However, there is also one report which suggests that $E^{ms}$ could be an important antigen for the protection of pigs against CSF (König et al., 1995, J. Virol. 69:6479–6486). In these studies, $E^{ms}$ was expressed with a live virus vaccinia vector. Animals vaccinated simultaneously by 3 different routes (intradermally, intravenously, and intraperitoneally) with $5 \times 10^7$ PFU of vaccinia-$E^{ms}$ recombinant virus per injection site, survived an IN challenge with a lethal dose of CSFV strain Alfort at 5 weeks post-vaccination, without showing any signs of CSF.

To evaluate the suitability of $E^{ms}$ as a dead subunit vaccine, baculovirus expressed $E^{ms}$ of strain Brescia (conform Hulst et al., 1994, Virology, 200: 558–565) was tested in pigs. Groups of 6 SPF pigs were vaccinated once IM with 5.0 and 20 μg $E^{ms}$, respectively (Moormann et al., 1996, Proc. 14th Intern. Pig. Vet. Society Congress, pp. 25–29, Bologna, Italy). A third group of 4 nonvaccinated SPF pigs served as control. Three weeks after vaccination all animals were challenged IM with $10^5$ $TCID_{50}$ of strain Behring. Within 5 days after challenge all animals vaccinated with the lowest dose $E^{ms}$ developed severe signs of CSF. Within 14 days after challenge, 2 animals died, 3 were killed when moribund, and 1 apparently recovered. Five of these animals, including the one that recovered, were positive in the IFT. After challenge, all animals vaccinated with the highest dose $E^{ms}$ showed, more or less, severe signs of CSF and high fever for several days, but within 14 days, 4 of 6 animals recovered, I animal had died, and another was killed when moribund. Of the 4 surviving animals, only 1 appeared positive in the IFT. In contrast, all control animals showed severe signs of CSF within 5 days after challenge, died within 14 days after challenge, and were positive in the IFT (Moormann et al., 1996, Proc. $14^{th}$ Intern. Pig. Vet. Society Congress, pp.25–29, Bologna, Italy).

We concluded that baculovirus expressed $E^{ms}$ can protect pigs against a heterologous CSFV challenge, albeit with a much lower efficacy than baculovirus expressed E2 does.

Follicle-stimulating hormone (FSH) belongs to the family of glycoprotein hormones, which are produced either in the pituitary (luteinizing hormone, LH; thyroid stimulating hormone, TSH) or in the placenta (human chorionic gonadotropin, hCG; pregnant mare serum gonadotropin, PMSG). Within a species, each of these hormones consists of a common alpha subunit, which is noncovalently bound to a hormone-specific beta subunit. Purified FSH, administered alone or in combination with LH, is widely used to induce a superovulatory response in many species, including cattle.

A problem in the cow is that bovine FSH is difficult to purify in substantial quantities from bovine pituitaries. For this reason, FSH of ovine (oFSH), porcine (PFSH) or equine (eFSH, PMSG) origin is commonly used for superovulation treatment of cows. However, application of brain tissue-derived material is not free of risk, due to the possible presence of prion-like proteins, which can cause bovine spongiforme encephalopathy (BSE) in cows, and possibly a variant of Creutzfeldt-Jacob disease (CJD) in humans. Furthermore, the use of placenta-derived material has the disadvantage of a very long biological half-life, which necessitates its neutralization by the injection of specific antibodies. Finally, all currently used FSH preparations do contain some LH activity which is considered responsible, at least in part, for the observed large variation in superovulation results.

For these reasons, it seems likely that superovulation treatment of cows can benefit from the application of recombinant bovine FSH (rbFSH) produced in nonmammalian cells, such as insect cells (baculovirus expression system).

MATERIALS AND METHODS

1. An example of the preparation of a production cell culture (PCS) of SF21 cells A cryo vial with 1.5 ml of SF21 working cell seed (WCS) (total number of cells is 4-10×106 cells/ml) is thawed to a temperature of 20–30° C. After thawing, the content of the vial is transferred to a 15 ml FALCON™ tube, containing 8.5 ml serum free medium SF900I, and suspended. After suspension, the content of the FALCON™ tube is centrifuged at 100–200 xg for 10 minutes to precipitate the cells. The medium is discarded and the pellet suspended in 4–6 ml of SF900II. The suspended cells are transferred to a 100 ml shake flask, containing 10 ml SF900II. The cells are cultured for 3–7 days at 26–30° C. by placing the flask on an orbital shaker platform at 40–80 rpm. Cell growth and cell viability are monitored by taking in process samples. When the cell density is 1.0–6.5×10$^6$ cells/ml, the cells are passed to two 500 ml shake flasks, containing 100 ml SF900II each. This corresponds to a 10-fold dilution of the cells. Again, the cells are cultured for 3–7 days at 26–30° C. by placing the flask on an orbital shaker platform shaking at 40–60 rpm. Cell growth and cell viability are constantly monitored by in-process control. When the cell density is 1.0–6.5×10$^6$ cells/ml, the cells are passed for a second time to, in this case, six to eleven 500 ml shake flasks, containing 100 ml SF900II each. Excess cell material is discarded. Also, in this case, a 10-fold dilution is achieved. The cells are cultured for 3—7 days at 26–30° C. by placing the flask on an orbital shaker platform shaking at 40–80 rpm. Cell growth and cell viability are constantly monitored by in-process control. When the cell density is 1.0–6.5×10$^6$ cells/ml, 500 ml or 1000 ml of the suspension containing the cells is passed to a 5 liter or 10 liter fermentor, containing approximately 4.5 liters or 9 liters of SF900II, respectively. This corresponds to a 10-fold dilution of the cells. The cells are cultured for 3–7 days at 26–30° C. The suspension is constantly stirred (50–100 rpm). Cell growth and cell viability are constantly monitored by in-process control. When the cell density is 1.0–6.5×10$^6$ cells/ml, the content of the 5 liter fermentor is passed to a 50 l fermentor, containing approximately 40 liters of SF900II. The cells are cultured at 26–30° C. until a density of ±5–15×10$^5$ cells/ml is reached. The suspension is constantly stirred (50–100 rpm). Samples are taken for in-process control.

2. An example of the production of E2 antigen

To the above-mentioned cell suspension, 1–2 ml of Working Seed Virus (WVS) (BacE2[-]) containing ±10$^7$ TCID$_5$/ml is added. The suspension is incubated at 28° C. for 3–8 days until 70–100% of the cells show a cytopathic effect. During the incubation, samples are taken for in-process control. Next, the suspension is clarified by removal of the cells by microfiltration. The obtained filtrate (i.e., the antigen solution) is collected and stored at ≤−20° C. until the inactivation step (3.3) is started. Samples are taken for in-process control. To determine antigen content or antigenic mass, samples are tested, e.g., in an enzyme-linked immune assay, or in a protein assay to determine actual weight per volume of the water protein, or by a combination of such methods.

3. An example of the virus inactivation

The virus is inactivated by adding 2-Bromoethyl-ammoniumbromide (BEA) to a concentration 10 mmol/l. By adjusting the pH to 8.2–8.7 and the temperature at 34–37° C., BEA is converted to 2-bromoethyl-imminebromide (BEI), which is the active component to inactivate the virus. Virus kill is checked by taking samples for in-process control. The inactivation takes 24–72 hours. After activation, <1 infectious particle per 10,000 liters may be present. After virus inactivation, BEI is neutralized by adding sodium-thiosulphate to a concentration of 5–25 mmol/1 and adjusting the pH to 5.7–6.3. Samples are taken for in-process control. The inactivated and neutralized antigen solution is transferred into 1 and/or 5 liter bags and stored at <−20° C.

4. An example of the formulation

The frozen antigen solution is thawed at 22–28° C. and diluted with SF90011 or PBS to an antigen solution of 50 μg/ml. Thiomersal is added as an anti-microbiological agent to 100 μg/ml. Samples are taken for in-process control. This solution (i.e., the first water phase) is stored at 2–8° C. for 3 days. Meanwhile, the oil phase has been prepared by mixing Marcol 52 with Montanide 80(9:1). This solution is also stored at 2–8° C. for no more than 3 days. The oil phase is sterile filtered through a 0.22 μm-sterile filter. Samples are taken for in-process control. Finally, the second water phase is prepared by mixing phosphate-buffered saline (PBS) or SF900II medium with Montanox 80 (98:2), and thiomersal is added to a final concentration of 100 μg/ml. This red at 2–8° C. until use (<3 days). Before use, the first water phase is sterile filtered. Samples are taken for in-process control. The first emulsion is prepared by mixing the first water phase with the oil phase (1:1.1). This emulsion may be stored at 2–8° C. no more than 3 days. Samples are taken for in-process control. The double water-in-oil emulsion is prepared by emulsifying the first emulsion with the second water phase (2.1: 1). The double emulsion is stored at 2–8° C. in a quarantine storage room until filling in vials. Samples are taken for in-process control.

5. An example of the filling and capping

The double emulsion solution is filled aseptically in a class A zone in the clean room. The filling volume is 51, 102 or 255 ml in 50, 100 or 250 ml vials, respectively. The filling volume is constantly monitored, by checking the weight of the filled volume. Immediately after filing, the vials are stoppered and capped. Finally, the vials are stored in a quarantine storage room at 2–8° C. after which the quality control is initiated.

Example of a scheme for 50 liters fermentor scale E2 subunit vaccine

Preparation of an SF 21 Production cell culture (PCS)

```
┌─────────────────────────────────────┐
│ Thaw (a) cryo vial(s) with 1.5 ml of│
│ 4–10 x 10^6 cells/ml of SF21 working│
│ cell seed (WCS) to 20–30° C..       │
└─────────────────────────────────────┘
                 │
┌─────────────────────────────────────┐
│ Transfer to a 5 ml FALCON™          │
│ tube containing 8.5 ml serum free   │
│ medium (SF900II) and suspend.       │
└─────────────────────────────────────┘
                 │
┌─────────────────────────────────────┐
│ Centrifuge 10 min. at 200–200x g.   │
└─────────────────────────────────────┘
                 │
┌───────────────┐
│ Discard medium│──────
└───────────────┘
                 │
┌─────────────────────────────────────┐
│ Resuspend pellet in 4–6 ml SF900II  │
│ and transfer to 100 ml shake flask  │
│ containing 10 ml SF900II.           │
└─────────────────────────────────────┘
                 │
┌─────────────────────────────────────┐
│ Culture cells during 3–7 days at 26–│
│ 30° C. to 1.0–6.5 x 10^6 cells/ml.  │
└─────────────────────────────────────┘
                 │
┌─────────────────────────────────────┐
│ Pass cell to two 500 ml shake flasks│
│ containing 100 ml SF900II (i.e., 10-│
│ fold dilution).                     │
└─────────────────────────────────────┘
                 │
┌─────────────────────────────────────┐
│ Culture cells during 3–7 days at 26–│
│ 30° C. to 1.0–6.5 x 10^6 cells/ml.  │
└─────────────────────────────────────┘
                 │
┌─────────────────────────────────────┐
│ Dilute cells 10-fold and pass cells to│
│ six to eleven 500 ml shake flasks   │
│ containing 100 ml SF900II.          │
└─────────────────────────────────────┘
                 │
┌─────────────────────────────────────┐
│ Culture cells during 3–7 days at 26–│
│ 30° C. to 1.0–6.5 x 10^6 cells/ml.  │
└─────────────────────────────────────┘
                 │
┌─────────────────────────────────────┐
│ Transfer 500 ml to a 5 l Fermentor, │
│ containing appr. 4.5 l SF900II or   │
│ 1000 ml to a 10 l fermentor         │
│ containing appr. 9 l SF900II.       │
│ Culture cells during 3–7 days at 26–│
│ 30° C. to 1.0–6.5 x 10^6 cells/ml.  │
└─────────────────────────────────────┘
                 │
┌─────────────────────────────────────┐
│ Transfer to a 50 Fermentor,         │
│ containing appr. 40 l SF900II.      │
│ Culture cells at 26–30° C. to a cell│
│ density of 5–15 x 10^5 cells/ml.    │
└─────────────────────────────────────┘
```

Production of E2 antigen

```
┌─────────────────────────────────────┐
│ Add 1–10 ml of Working Seed         │
│ Virus (WSV), containing ± 10^7      │
│ TCID_{50}/ml.                       │
└─────────────────────────────────────┘
                 │
┌─────────────────────────────────────┐
│ Incubate at 28° C. (3–8 days)       │
│ until 50–100% of the cells show     │
│ Cytopathic effect (CPE).            │
└─────────────────────────────────────┘
                 │
┌─────────────────────────────────────┐
│ Remove cell material by micro       │
│ filtration                          │
└─────────────────────────────────────┘
                 │
┌──────────────┐        ┌──────────────┐
│ Discard      │        │ Sterile      │
│ concentrated │────────│ filtration   │
│ biomass      │        │              │
└──────────────┘        └──────────────┘
                 │
┌─────────────────────────────────────┐
│ Store antigen solution at 4° C.     │
└─────────────────────────────────────┘
```

Virus inactivation

```
┌─────────────────────────────────────┐
│ To inactivate the virus, add 2-     │
│ Bromoethyl-ammoniumbromide (BEA)    │
│ to a concentration of 8–12 mmol./l. │
└─────────────────────────────────────┘
                 │
┌─────────────────────────────────────┐
│ Adjust the pH to 8.2–8.7 and incubate│
│ for 24–72 hours at 34–39° C.        │
└─────────────────────────────────────┘
                 │
┌─────────────────────────────────────┐
│ To neutralize BEI, add 0.8 mol.l    │
│ Sodium-thiosulphate to a final      │
│ concentration of 5–25 mmol/l.       │
└─────────────────────────────────────┘
                 │
┌─────────────────────────────────────┐
│ Adjust the pH to 5.7–6.3.           │
│ Control inactivation and            │
│ neutralization.                     │
└─────────────────────────────────────┘
                 │
┌─────────────────────────────────────┐
│ Transfer inactivated and            │
│ neutralized antigen solution into   │
│ 1 and/or 5 l. bags and store at     │
│ ≤ -20° C..                          │
└─────────────────────────────────────┘
```

Formulation

Prepare the oil phase by mixing Marcol 52 and Montanide 80 (9:1). The mix is sterile filtered (0.22 μm). Store at 2–8° C.

Thaw the frozen antigen solution at 22–28° C.

Prepare the first water phase by mixing the thawed antigen solution with SF900II to 50 μg antigen/ml. Add thiomersal to 100 μg/ml. Store at 2–8° C..

Prepare the second water phase by mixing PBS with Montanox 80 (0.98:0.02) and thiomersal to a final concentration of 100 μg/ml. The phase is sterile filtered (0.22 μm). Store at 2–8° C..

Prepare the first emulsion by mixing the oil phase and the first water phase (1.1:1). Store at 2–8° C..

Prepare the double emulsion by mixing the first emulsion with the second water phase (2.2:1). Store at 2–8° C..

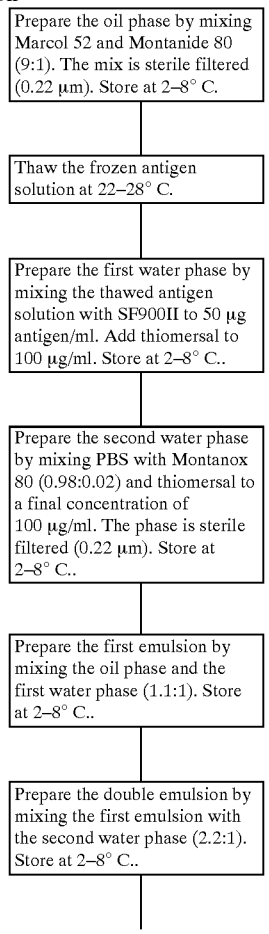
Filling and capping
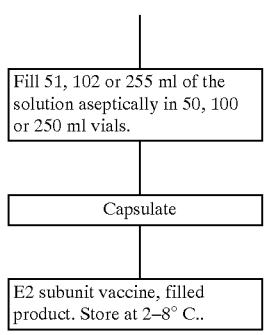

Fill 51, 102 or 255 ml of the solution aseptically in 50, 100 or 250 ml vials.

Capsulate

E2 subunit vaccine, filled product. Store at 2–8° C..

6. An example of an E2 stability experiment
Purpose

To investigate the stability of the E2 protein in an infected cell culture (MOI*0.0001) after prolonged culturing under otherwise normal conditions. Due to the lytic nature of the infection process of the baculovirus in the cell culture, proteases might be released in the medium late in the infection cycle. Whether or not this results in degradation of the E2 protein and, thus, in a decrease of the volumetric E2 protein levels, is the topic of this experiment.

Materials and methods

When medium or SF900II is mentioned, SF900II medium with 0.2% Pluronic F68 is meant.

A vial with SF21 cells is thawed and cultured in 10 ml of SF900II in a 100 ml shake flask in an incubator on an orbital shaker platform. When the cell culture reaches the required cell density, the cells are diluted ten-fold to 100 ml in a 500 ml shake flask. When this cell culture reached the required cell density, it was passaged by diluting ten-fold to 100 ml again. Excess cell material was discarded. When this cell culture reached the required cell density, it was diluted ten-fold to three 500 ml shake flasks with 100 ml volume per flask. Excess material was discarded. The shake flasks are placed on an IKS orbital shaker platform, stirring at 70 rpm in an 28° C. incubator.

At a cell density of 0.612*105 cells per ml, 63 μl of a 100× diluted virus suspension is added to flask nos. 2 and 3. Shake flask no. 1 is kept as an uninfected blank. The MOI with which the cultures are infected is (0.063*0.01*0.8*107)/(100*0.612*105)=0.00008.

The 100× diluted virus suspension that was used was prepared as outlined below. MSV vial 253 was thawed by QC and diluted 100× in TC100 medium, supplemented with 10% FBS (lot no. 97QC0139) and stored at −70° C. in 0.5 ml portions.

Regularly, samples are taken from both infected shake flask cultures and the uninfected shake flask for determination of the condition of the cell culture. Sampling was performed as outlined below.

Approximately 1.1 ml of cell material is spun down in 15 ml FALCON™ tubes in IEC Centra GP8R centrifuge for 6 minutes at 1000 rpm. Then the supernatant is 0.45 μm filtered through a Gelman ACRODISC® syringe filter to discard cells that might still be present. 0.4 ml samples are stored in NALGENE cryogenic vials at −70° C. for later analysis.

Results and conclusions

As can be seen in the data in FIG. 1 and the graphs in FIG. 2, the cell growth curves in flasks 2 and 3 develop more or less similarly. After 191 hpi, no more cell counts were done, since virtually all cells were dead and infected. The 139 hpi sample of flask 2 is left out of the graph. The cell counts of this sample are much higher than both the previous and following sample. This indicates that probably some precipitation has occurred before or after sampling resulting in an inaccurate sample that was mixed with the trypan blue solution. This assumption is confirmed by the fact that both the viability and infection percentage are in accordance with expected results. This means that nothing unusual is happening in the infected culture itself. This inaccurate sampling will most likely have no effect on the E2 concentration in the sample, since the E2 is present in the medium and not intracellular.

The E2 concentration in flask 2 rises quite rapidly to a maximum of >190 μg/ml around 139 hpi and then slowly decreases to 170 μg/ml at 215 hpi. Then the E2-content drops more quickly to a final level of <100 μg/ml at 306.5 hpi.

The profile in flask 3 is more or less the same. The maximum E2 protein content is also reached around 139 hpi, but it is slightly higher than in flask 2. The E2 concentration slowly decreases from 233 μg/ml at 139 hpi to 212 μg/ml at 191 hpi before the concentration drops more rapidly to 141 μg/ml 215 hpi. Flasks 2 and 3 show a good correlation.

At t=44.25 hpi shake flask no. 1, the blank, was also counted. Living cell density was 2.435*106 cells/ml, dead cell density 0.190*106 and total cell density 2.625*106 cells/ml, giving a viability of 92.8%. The living cell density is significantly higher than in both flasks 2 and 3, indicating that infection is already slowing down cell growth. This blank culture was subsequently passaged.

The following table shows the results of immunoblotting assay performed on a selection of flask 2.

| Sample (hpi) | V3 | Degraded V3 | V8 | Degraded V8 |
|---|---|---|---|---|
| 0 | − | − | − | − |
| 44 | − | − | − | − |
| 115 | + | − | − | − |
| 139 | + | − | + | − |
| 164.5 | + | − | + | − |
| 191 | + | + | + | − |
| 288 | + | + | + | + |
| 306.5 | + | + | + | − |

"−" indicates not detectable, "+" indicates detectable

As can be seen in this table, epitopes V3 and V8 are not yet detectable in the 0 and 44 hpi samples. This correlates well with the results of the E2-ELISA. In the samples from 115 hpi onwards, intact E2 is detected, since both V3 and V8 are detected in the E2 band.

From 191 hpi onwards, a second band from a smaller protein is visible on the gel. Immunoblotting with V3 and V8 in two separate blots shows that the degradation product does contain the V3 epitope but not the VS epitope. No VS is detected anywhere else on the blot but in the intact E2 band. This assay clearly shows that degradation of the E2 protein does occur due to the presence of proteases. In fact, this may be held responsible for the drop in the E2 protein content which is observed during the microfiltration step of the bulk E2 antigen solution. In this downstream processing step, cells are removed before the virus inactivation starts.

Therefore, it is most likely that the presence of a protease causes the degradation of the E2 protein.

7. An example of an MOI experiment

Purpose

To further investigate the relationship between MOI (multiplicity of infection, number of viruses per cell) maximum cell density and volumetric E2-content, on the one hand, infection of the complete cell population must be completed before the medium is exhausted, but on the other hand, infection of the total population at low cell concentration results in suboptimal protein yields.

Materials and methods

When medium is mentioned, SF900II medium is meant.

76 ml of cell suspension was diluted in 444 ml SF900II in a 1000 ml bottle and gently mixed. The living cell density just before dilution of the culture was $3.41*10^6$ cells/ml, the dead cell density $0.190*10^6$, giving a viability of 94.8%. This dilution should give a cell density of $±5*10^5$ cells/ml.

Furthermore, gentamycin was added to a final concentration of 10 $\mu$g/ml. The cell suspension was divided into nine 50 ml portions in 250 ml shake flasks and excess cell material was discarded. The first 50 ml was transferred to shake flask 1, the final 50 ml to shake flask 5.

nos. 1 and 6 are used for MOI=0 (blank),
nos. 2 and 7 for MOI=0.000001,
nos. 3 and 8 for MOI=0.00001
nos. 4 and 9 for MOI=0.0001
no. 5 for MOI=0.001

The preparation of the virus stock is as follows: a dilution range is made of a vial with 100× diluted virus suspension (the vial contains $0.8*10^5$ plaque forming units (pfu) per ml). This 100× diluted virus stock solution was prepared as follows:

Master seed virus was thawed and diluted 100× in TC100 medium, supplemented with 10% FBS and stored at −70° C. in 0.5 ml portions.

0.4 ml of this 100× diluted virus solution is diluted with 3.6 ml of SF900II medium, resulting in a dilution factor of $10^{-1}$. 1 ml of this solution is added to 9 ml of medium, resulting in a dilution factor of $10^{-2}$, 1 ml of this solution is added to 9 ml of medium to give a dilution factor of $10^{-3}$ and 1 ml of this solution is diluted ten-fold to give a dilution factor of $10^{-4}$. 3.1 ml of medium is added to shake flasks 1 and 6 (blank flasks), containing the cell culture. 3.1 ml of virus dilutions $10^{-2}$, $10^{-3}$ and $10^{-4}$ are added to shake flasks 4 and 9, 3 and 8, and 2 and 7, respectively. These shake flasks already contain the cell culture.

In 3.1 ml of virus dilution $10^{-2}$ there are $3.1*10^{-2}*0.8*10^5=2.5*10^3$ pfu present. In a shake flask with 50 ml of cell suspension, $0.5*10^6*50=2.5*10^7$ cells are present. So, addition of 3.1 ml of virus dilution $10^{-2}$ to 50 ml of the cell suspension results in an MOI of $2.5*10^3/2.5*10^7 = 0.0001$. Making comparable calculations for the other virus dilutions, MOI counts of 0.00001 and 0.000001 are obtained for virus dilutions $10^{-3}$ and $10^{-4}$ added to 50 ml of cell culture. Finally, 2.85 ml of dilution $10^{-1}$ is added to shake flask no. 5, resulting in an MOI of 0.00092 instead of 0.001.

A 3.1 ml sample is taken of each shake flask immediately after virus addition. The cells in the samples are spun down in an IEC Centra GP8R centrifuge in 15 ml FALCON™ tubes (10 min 1000 rpm). Sampling is carried out going from low MOI to high MOI to prevent virus transmission from an infected cell suspension with high MOI to a cell suspension infected with low MOI. After centrifugation, samples are 0.45 $\mu$m filtered (to remove cells that might still be present in the supernatant) and divided over 3 NALGENE cryovials and stored at −70° C. for testing later on.

The cell density of shake flasks 1 and 5 was determined immediately after virus addition. These were the first and the last flask to be inoculated with cells. Since the cell densities were almost identical, it was assumed that all flasks had a cell density equal to the average value of both cell counts. The initial living cell density was $0.423*10^6$ cells/ml, whereas $0.012*10^6$ cells were dead, giving a viability of 97.3%.

All flasks were placed on the Labotech 300 orbital shaker platform, stirring at approximately 75 rpm in the 28° C. room.

At 23, 95, 125, 144, 173 and 194 hpi (hours post infection) all flasks were sampled. Samples from which the cell density was determined had a volume of 3.3 ml, of which 0.2 ml was used to determine the cell density. The remaining 3.1 ml is handled as mentioned above for the t=0 sample. Samples of cultures that were not counted had a volume of 3.1 ml. At 194 hpi, the cell density was determined and the experiment was terminated. The remaining cell suspension (approximately 30 ml) was stored in 3 portions of 1 ml in NALGENE cryovials and 4 portions of approximately 6 ml in 15 ml FALCON™ tubes.

Results and conclusions

The results show that there is a good correlation between MOI and optimum cell density and, more importantly, between MOI and E2 protein yield. This can be seen in the graphs where the maximum volumetric E2 protein yield of the cultures infected with MOI 0.001 is set at 100%. It shows that the volumetric E2 protein yield increases with decreasing MOI. Up to an MOI of 0.0001, the cell density is infected before the maximum achievable cell density is reached. Using an MOI of 0.00001 or less, results in an infection where the medium is exhausted before the infection of the culture is completed, resulting in suboptimal protein yields.

The conclusion can, therefore, be drawn that the lower the MOI used, the higher the E2 protein yield, provided that the medium is not exhausted before the infection process and E2 production is completed.

Recombinant baculoviruses expressing bFSHα and/or bHSFβ

Transfer vectors pDW-Alpha-9.1 and pDW-Beta-3.1 were constructed. Sf21 cells were co-transfected with pDW-Alpha-9.1 or pDW-Beta-3.1 and wild-type (wt) AcNPV/M021 DNA isolated from extracellular virus particles (PCT application: Wo 96/25696). Polyhedrin-positive plaques expressingβ-galactosidase were isolated and analyzed for expression of bFSHα or bFSHβ by ELISA of culture media. One plaque-purified bFSHct virus (AcNPVα3.4) and one plaque-purified bFSHβ virus (AcNPVβ1.4) were used to prepare virus stocks with a TCID50 of approximately $10^7$ and $10^{8,}$ respectively. Production of FSH occurred according to the methods described above and resulted in production levels varying from 17 to 33 μg/ml.

$PD_{95}$ Trial

Assessment of the dose (μg) of E2 needed after one vaccination to protect 95% ($PD_{95}$) of the vaccinated pigs against a challenge with a 100 $LD_{50}$ of the virulent CSFV strain Brescia.

Animals

Twenty-six specific-pathogen-free (SPF) pigs, 6–7 weeks old, were randomly divided on arrival in three groups of eight (A–C) and one group of two (D). The animals were housed in stables B18, B19, B20 and B21 within the high containment facilities of the ID-DLO. The animals were left to acclimatize for three days. The animals were fed once a day, in a trough, with complete food pellets (Hope Farms), and could drink water from a nipple ad libitum.

Vaccination and challenge

Three formulations of double-water-in-oil adjuvanted vaccine were prepared as described above, each with a different concentration of E2 antigen; 32.0, 8.0 and 2.0 μg/dose. The pigs were inoculated once intramuscularly, each pig receiving one dose, 2 cm behind the left ear (A: 2 μg E2; B: 8 μg E2; C: 32 μg E2; D: 0 μg E2). The control group D was inoculated with DOE adjuvant only and the sentinel pigs were not inoculated at all. Three weeks after vaccination, each animal, except the sentinels, was challenged intranasally with 100 50% lethal doses (=100 Va $LD_{50}$) of CSFV strain Brescia 456610. Just before challenge, the sentinels were separated from their group and returned 24 hours later. Viral contents of the inoculum was determined by titration of a sample taken after return from the stable.

Clinical observation

The pigs were checked daily by the animal technicians, abnormal findings were recorded and, if necessary, the supervising veterinarian was called. Each group was observed at least 15 minutes per day before and during feeding time and cleansing of the stable.

A reduction in food uptake of the group or an individual animal was noted.

Body temperatures (rectal) were recorded during nine days after vaccination and for 20 days after challenge.

Blood analysis after challenge

EDTA-blood samples were collected on day 0, 2, 4, 7, 10 and 14 after challenge to monitor changes in leucocyte and thrombocyte numbers. A decrease in the number of leucocytes (leucopenia) and thrombocytes (thrombocytopenia) in the blood is one of the typical signs of CSF. Normal cell counts for white blood cells and thrombocytes in conventional swine range between,. respectively, 11–23 $10^9$/l and 320–720 $10^9$/l. For SPF pigs, these values are a bit lower, 6–12 $10^9$/l and 300–700 $10^9$/l. Both mentioned ranges vary in each pig. The blood cell analyses were performed with a MEDONIC® CA 570 coulter counter. Leucopenia and thrombocytopenia were defined as cell/platelets counts, considerably lower than the minimum number mentioned above, preferably for more than one day.

Virus spread/excretion and viral detection

The temperature, leucocyte and thrombocyte counts, and seroconversion of the sentinels were the parameters used to detect virus transmission from the inoculated animals to these animals. At post-mortem, tissue samples were collected from the following organs: tonsil, spleen, kidney and ileum. They were tested by direct immunofluorescent technique for the presence of viral antigen. Cryostat sections (4 μm thick, two per organ) from these tissue samples were fixed and incubated with a polyclonal swine anti-pestivirus FITC-conjugated serum. After washing, the sections were read under a fluorescent microscope. Results were expressed as positive (=fluorescence) or negative (=no fluorescence).

Serological response

Serum of all pigs was collected at 0, 2 and 3 weeks post-vaccination and at death.

Samples were stored at −20° C. and assayed in a virus neutralization test (VNT) and the CEDITEST® CSFV ELISA, an ELISA for detecting CSF-specific antibody. CSFV-neutralizing antibody titres in serum were determined in a microtitre system. Serial two-fold dilutions of serum were mixed with an equal volume of a CSFV (strain Brescia) suspension which contained 30–300 $TCID_{50}$. After incubation for 1 hour at 37° C. in a $CO_2$ incubator, approximately 25.000 PK 15 cells per well were added. After four days, the microtitre plates were treated as mentioned above and read microscopically. The CSFV-neutralizing titre was expressed as the reciprocal of the highest dilution that neutralized all virus.

Statistical evaluation

Determination of the 95% protective dose was based on the assumption that a CSFV neutralizing Ab titer of ≥50 stands for full protection.

RESULTS

For animal numbers throughout this section compare tables 1 or 2.

Clinical observation after vaccination

Vaccination did not have any adverse effect on the pigs, food uptake and body temperature remained normal. Among groups A and C, mild diarrhea, anorexia and depression was seen on day 3 after vaccination. One pig from group A (no. 448) vomited regularly during the whole period and stayed behind in growth. Pig no. 438 from group B vomited once. The temperature of pig no. 434 (group C, sentinel) was slightly elevated; this animal was suffering from lameness of the right hind leg. Food uptake increased during the period between vaccination and challenge from 3 to 6 kg per group/day.

Clinical observation after challenge

Unvaccinated control animals developed signs of CSF on three (no. 59) and six (no. 60) days after challenge: fever, huddling, shivering, loss of appetite and depression were seen till death, 10 days after challenge. Furthermore, the animals developed cyanosis, paresis posterior, diarrhea and severe vomiting. Both animals were killed, being moribund.

All the pigs vaccinated with 2 μg of E2 (group A) developed signs of disease 2–3 days after challenge, consisting mainly of fever, huddling, depression and anorexia. Fever lasted from 2–10 days and maximum temperatures ($T_{max}$) varied from 40.7–42.2° C. From day seven onwards among pigs 443–446, fever disappeared and the food uptake increased towards the amount before challenge. But pig 448 was found dead on day nine and pig 447 developed acute CSF (convulsions, paresis posterior) and was killed when moribund on the same day. Both sentinels remained normal until day 7–9 after challenge, after which they developed acute CSF and were killed when moribund on day 20.

In the animals of groups B and C, clinical signs and duration of disease were more mild as the payload of E2 antigen increased.

In group B (435–439), fever lasted to day 27 and $T_{max}$ varied between 40.2 and 41.7° C. Pig no. 436 resisted the challenge with very mild clinical signs. One pig (no. 440) died from acute CSF after 18 days, killed moribund. The remaining five animals from group B recovered. Both sentinels remained normal until day 11–12 after challenge, after which they developed acute CSF and were killed on day 20.

In group C, mild fever was seen in two (430, 431) out of six animals from day 4–6 and $T_{max}$ varied from 40.5–41.2° C. No clinical signs were noted except slight depression on day six after challenge. As before challenge, pig no. 430 vomited.

Both sentinels remained normal until the end of the experiment.

Blood analysis after challenge

From group A, only one pig (450), the sentinel, developed clear leucopenia and thrombocytopenia. Pig nos. 445 and 446 were thrombocytopenic on day 7 and 10 after challenge, pig 449 on day 10 and 14. One pig (440) from group B developed leucopenia and thrombocytopenia, the others remained normal. Both sentinels showed signs of a developing thrombocytopenia on day 14. Leucopenia and thrombocytopenia were not detected in group C, including the sentinels.

Both control animals (nos. 59 and 60) became thrombocytopenic from day 7 onwards.

Virus spread and viral antigen detection after challenge

Back titration of the inoculum rendered a virus titre of 2.55 TCID50/ml after return from the stable. CSFV viral antigen (Table 1) was detected in all of the selected tissue samples of the controls and sentinels from groups A and B. One out of six inoculated animals was positive in groups A and B, and none in group C, including the sentinels.

Serological response

Seroconversion for CSFV was defined as a titre ≥25 in the VNT. The result of the backtitration, in order to determine the amount of Brescia virus used in the VNT, was 41 TCID50/well.

None of the controls (D) or sentinel animals seroconverted during the experiment (table 2). Two out of six animals from group A had seroconverted after three weeks. Four out of six animals boostered after challenge (table 2). Groups B and C had seroconverted on day 21 after vaccination and all the animals boostered after challenge, the latter only indicating a successful replication of the challenge virus in the animal.

Conclusion

The $PD_{95}$ dose per animal was determined as 32 μg of E2 in 2 ml of DOE adjuvant given once. With this dose, clinical signs of disease after a challenge with a highly virulent CSFV strain remained minimal and no spread of virus to contact animals occurred. In summary, four groups (A–D) of six pigs were vaccinated by intramuscular route with, respectively, 32(A), 8(B), 2(C) and 0 μg Ed (D) per 2 ml adjuvant (DOE). Two nonvaccinated pigs were kept within each group (A–C) to detect virus excretion causing contact infections (sentinels). After three weeks, the animals were challenged by intranasal route with 100 $LD_{50}$ of the highly virulent CSFV strain Brescia. Clinical, virological and serological parameters were measured in order to assess the efficacy of this E2 sub-unit vaccine. As expected, animals in group C resisted the challenge better than the animals from the other groups. No viral antigen was detected in tissue samples from the animals inoculated with the highest dose of E2 (32 μg) and disease was absent in this group. The $PD_{95}$ dose was calculated on the assumption that an NPLA titre of ≥50 (on 21 days after vaccination) gives full protection (no spread of virus). This resulted in a $PD_{95}$ dose of 32 μg/animal.

To further assess the level of protection against a challenge with 100 $LD_{50}$ virulent CSFV at 2 and 3 weeks after vaccination, two groups (A–B) of six pigs were vaccinated by the intramuscular route with 32 μg of E2. Two nonvaccinated pigs were kept within each group (A–B) to detect virus excretion from the vaccinated pigs causing contact infections. After two (A) and three (B) weeks, the vaccinated animals and control animals were challenged by intranasal route with 100 $LD_{50}$ of the highly virulent CSFV strain Brescia. Clinical, virological and serological parameters were measured in order to assess the efficacy of the E2 subunit vaccine two and three weeks after vaccination. As expected, group B resisted the challenge with less clinical symptoms than group A. Transmission of virus to the sentinels occurred only in group A and in the leucofractions of all the animals from both groups virus was detected. Only one animal in group B had seroconverted on day 14 after vaccination (no. 414). From the same group, one animal had not seroconverted after 21 days but was protected, had fever for only two days, and seroconverted within eleven days after challenge. Only the controls and one of the sentinels (group A) developed leucopenia and thrombocytopenia. No viral antigen was detected in any of the tissue samples from the animals of groups A and B. Concluding, all animals were protected against the challenge at two and three weeks after vaccination with a single dose.

To further assess the level of protection against a challenge with 100 $LD_{50}$ virulent CSFV at 3 and 6 months after vaccination, two groups (A–B) of six pigs were vaccinated by the intramuscular route with 32 μg of E2. Two nonvaccinated pigs were kept within each group (A–B) to detect virus excretion from the vaccinated pigs causing contact infections. After three (A) and six (B) months, the vaccinated animals and control animals were challenged by intranasal route with 100 $LD_{50}$ of the highly virulent CSFV strain Brescia. Clinical, virological and serological parameters were measured in order to assess the efficacy of the E2 subunit vaccine after this period. All the animals from group A and B resisted the challenge with minor clinical symptoms. Only the controls developed leucopenia and thrombocytopenia. Transmission of virus to the sentinels did not occur. Virus was not detected in any of the leucofractions selected from both groups. Only one animal in group B had seroconverted on day 28 after vaccination (no. 1983). No viral antigen was detected in any of the tissue samples from the animals of groups A, B and the sentinels. In conclusion, all animals were protected against the challenge on three and six months after vaccination with a single dose, and virus transmission did not occur.

BVDV strains 4800, 150022 and 178003 were used to generate experimental E2 subunit vaccines. The E2 genes of these strains were expressed in the baculovirus expression system (Hulst et al., 1993, J. Viral. 67: 5435–5442; P. A. van Rijn et al., 1996, I; Gen. Virol., 77: 2737–2745). The Spodoptera frugiperda cell line, SF21, was used for propagation of the recombinant baculoviruses and the production of E2 proteins. SF21 cells were grown at 28° C. in serum free SF900 medium (GIBCO BRL). Confluent monolayers of SF21 cells were infected with recombinant baculovirus at a multiplicity of infection of 5 $TCID_{50}$ (50% tissue culture infective dose) per cell. After 4–5 days, the cultures showed a cytopathic effect of 80–90%. The cells were centrifuged for 10 minutes at 1500* g and the supernatant, containing baculovirus and E2, was collected and stored at −20° C. To inactivate baculovirus, a 2-bromoethyl-imminebromide (BEI) treatment was performed according to standard procedures. Briefly, 600 µl BEI and 600 µl 1 M NaOH were mixed. After 30 minutes at 20° C., 150 ml supernatant was added and stirred for 24 hours at 20° C. Then, 20 ml of 25% thiosulphate was added. Inactivation of the baculovirus was confirmed by titration of the supernatant on SF21 cells.

Experimental BVDV vaccines consisted of the supernatants containing E2 in a double water-oil emulsion. The oil contained 90% Marcol 52 (Esso) and 10% Montanide 80 (Seppic). The water fraction (PBS+) contained 98% phosphate-buffered saline, 2% Montanox 80 (Seppic) and 100 ppm thiomersal. Supernatant, oil and PBS+ were used in the proportion of 10:11:10. First, supernatant and oil were emulsified and then PBS+ was added and emulsified. A control vaccine was similarly prepared of the supernatant of SF21 cells infected with wild-type baculovirus. After preparation, the vaccines were found to be sterile.

Our preliminary assumption that the antigen amount in the 3 vaccines would be similar because of the comparability of the expressed proteins, was incorrect. The differences in antigen amount are probably caused by differences in expression in the insect cells. Vaccine 150022 contained 55 µg of E2 per dose and was protective for the fetus after 2× vaccination (day 0, and day 21). (Brusche et al. 1997, Vaccine in press.) Vaccine 4800 and vaccine 178003 contained 12 µg and 17 µg of E2 per dose, respectively, and were not protective for the fetus. This result suggests a correlation between the amount of E2 protein and fetal protection. However, a difference in immunogenicity of E2 glycoproteins and inability of the challenge strains to cross the placenta may also account for the different outcomes of the challenge. None of the vaccines protected against heterologous BVDV challenge.

The results of this study are promising for further development of BVDV subunit vaccines, since we have shown that fetal protection can be achieved by vaccination with envelope glycoprotein E2. Furthermore, it is a marker vaccine which allows discrimination between vaccinated animals and animals infected with a field virus strain. This is advantageous in the light of future BVDV eradication programs.

Discussion

The developed production process is aimed at achieving optimal heterologous protein production encoded by genes inserted into baculovirus in insect cells. The Baculovirus Expression Vector System (BEVS) is very well suited for producing different recombinant proteins, since correct protein folding and accurate post-translational processing results in biologically active proteins for animal and human applications. The baculovirus contains 2 nonessential genes, which are transcribed from very powerful promoters, the p10 and the polyhedrin promoters. Deletion mutagenesis of the p10 gene (van Oers et al., J. Gen Virol. 74: 563–574; 1993) showed that it is not essential for virus replication in cell culture. p10, however, is playing a role in cell lysis. Absence of the p10 protein causes the infected cells to remain intact and prevents the release of polyhedra from infected cells, thereby reducing reinfection rates but not infectivity, per se. The products of the genes (P10 or fibrillin and polyhedrin) are expressed late during the infection phase. Replacing these genes by the gene of the required protein can (in the case of the polyhedrin promoter) theoretically result in yields of up to 50% of total protein production of the insect cell culture, resulting in expression levels of over 1 gram polyhedrin protein per liter in culture (Maiorella et al., (1988) Large-scale insect cell culture for recombinant protein production, Bio/technology, 6, 1406–1410). The multiplicity of infection (MOI, ratio of virus density per ml and cell density per ml) is a key parameter for the optimization of the protein production. An obvious reason for infection with a low multiplicity of infection is to keep the virus inoculum as small as possible. If the infection takes place at a density of 2 million cells per ml at an MOI of 0.1 in a 50L fermentor, then $1 * 10^{10}$ viruses are needed. This would require an inoculum of around 1 liter. Furthermore, an extra production step is needed to make such an inoculum. Two major drawbacks of attached cultures are the inefficient medium usage and oxygen limitation. Due to the fact that the solubility of oxygen in aqueous fluids is relatively poor, oxygen will be the limiting substrate for the cells in monolayer cultures. The determining factor for maximum cell density in static cultures is the available surface. Once the surface is covered with a monolayer of cells, cell growth will come to a halt. This results in a cell density of approximately $1 * 10^6$ cells/ml medium. In suspension cultures, no oxygen limitation is present and the availability of other substrates is the limiting factor for cell density. This limitation occurs at a higher cell density than oxygen limitation and, therefore, the cell density becomes higher than in static cultures. Oxygen limitation is prevented by using an oxygen electrode to monitor the dissolved oxygen concentration. Once it drops below a certain value, oxygen is automatically added to the suspension, either by sparging or by addition via the head space of the fermentor. Moderate stirring of the suspension guarantees a homogenous culture in which no substrate gradients are built up and in which the cells are not subjected to too high shear forces. Furthermore, stirring results in an efficient transfer of viruses from infected to noninfected cells, giving a higher efficiency of virus infection of cells. Since initially only about 0.1–0.3% of the cells are infected, the remaining 99.7–99.9% of cells are allowed to grow and multiply. Virus particles that are produced in the infected cells are released 12–20 hours post-infection (Dee, K. U. and Shuler, M. L. 1997. Biotechnology Progress, 13, 14–24). The number of released virus particles per cell is 100–200, which can infect hitherto noninfected cells in a new cycle. It will take several cycles before enough virus particles are produced to infect all cells present in the culture. The aim is to complete the protein production of the final infection passage before the medium is exhausted and all metabolic processes come to a halt. It is also undesirable to achieve complete infection at a cell density that is suboptimal, for then the medium will not be used efficiently, resulting in a lower volumetric yield of the heterologous protein. The whole process of virus infection can be checked visually, due to the fact that the polyhedrin gene is still present. Virus infection can be observed as dense protein particles that accumulate in the cell nucleus. To prevent shear damage to the cells, Pluronic F-68 is added to the medium to a final concentration of 0.2%. Furthermore, if necessary, antifoam A is added to prevent excessive foaming, which also results in cell death. The total amount of antifoam A added to a 50L culture is on average 20 ml. The optimal virus density to infect the cells can be calculated. This density depends on the growth rate of the cells, the time post-infection at which the new virus particles are released, and the number of new virus particles produced per infected cell. Illustrating the method provided by the invention is the production of the pestivirus E2 protein. Although this protein was known as a potent antigen, E2 fragment production for a vaccine or a diagnostic test is not always successful. Despite a PD50 as low as 2 μg (when using a particularly immunogenic E2 fragment), a problem is how to accrue sufficient amounts of vaccine doses with sufficient antigenic mass in a commercially attractive way to enable protective vaccination of large groups of animals by one single vaccination per animal. This is particularly relevant for CSFV vaccination. When applied, CSFV vaccination generally is performed during a mass campaign in an area where an outbreak of OSFV has occurred. This asks for rapid vaccination of large numbers of animals in a relatively short period. In such a mass campaign, it is of imminent importance that an adequate protection level (the number of pigs that are protected against the wild-type virus infection) is achieved rapidly. Waiting for several weeks after a first vaccination for a second vaccination in order to achieve protection greatly hampers and delays the control of the disease. Differences between various methods to produce the recombinantly expressed E2 protein, even when comparing E2 fragments expressed in baculovirus, exist. In earlier reported E2 protein production cultures, the E2 protein fragment yield varied between 20–90 μg/ml (Hulst et al., J. Vir. 5435–5442, 1993; Hulst and Moormann, Cytotechnology 20:271–279, 1996), further necessitating immunoaffinity-purification with monoclonal antibodies to obtain the necessary and relevant E2 antigenic mass for single shot vaccination. Another method (using a fragment of E2 described in EP 0389034), which uses E2 harvested from the supernatant of insect cells without further immunoaffinity purification, results in an E2-based vaccine that is injected twice before a satisfying (protective) immune response is obtained. These problems, among others, relate to a low concentration of the relevant antigenic substance, in this case the E2 protein fragments, in the starting material, e.g., the cell culture supernatant, from which the vaccine is prepared. In theory, one can further accumulate antigenic mass by purification and condensation methods known in the art; however, this does not lead to a commercially attractive vaccine production but causes high costs per dose. Production runs using a method provided by the invention in our 50L fermentor routinely results in a yield of around 200–300 μg/ml CSFV E2 protein fragments, enough to theoretically vaccinate 100,000 animals per culture. Cells are infected at a density of 0.5 to $1.5*10^6$ cells/ml with 1 to 10 ml virus inoculum containing approximately $10^7$ $TCID_{50}/$ ml. The culture is preferably harvested when >50–80% of the cells show CPE. This is about 100–150 hours post infection. In earlier E2 protein production cultures, cells were synchronously infected with an MOI>1, resulting in a three-fold lower protein yield than as provided by the present invention. In a method provided by the invention, a 50L fermentor is inoculated with 5 L of cell suspension grown in a 5 L fermentor or 10L of all suspension, grown in a 10 L fermentor. The initial cell density is around $3*10^5$ cells/ml. Cells are grown to the calculated cell density before virus is added to the suspension. Downstream processing starts with the removal of the cells and polyhedra by microfiltration. A hollow fiber microfiltration device is connected to the fermentor and the material is pumped through the filtration module with a pore size of 0.22 μm. The retentate flow is recirculated over the fermentor and the permeate flow is collected in a 100 L vessel. When filtration is completed, the antigen solution, which is now cell-free but still contains infectious baculoviruses, is inactived in the 100 L vessel. Generally, 2-bromoethyl-ammoniumbromide (BEA) is added to the suspension to a final concentration of 8–12mM. The pH is raised from about 5.8 to 8.2–8.7 by adding 2M NaOH. This pH shift converts BEA to BEI (2-bromoethyl-imminebromide). This is the DNA-inactivating agent. pH is carefully monitored and regulated at 6–10 and the temperature is kept at 34–39. After 6 hours of inactivation, the antigen solution is transferred to a second inactivation vessel. This ensures that all material in the vessel has been in contact with BEI and thus will be inactivated. Drops of fluid-containing virus, but not containing BEI, could be present in the first vessel, but not in the second. Baculoviruses present in a concentration of $10^4$–$10^7$ pfu/ml are degraded to a value <$10^{-7}$ pfu/ml (<1 virus particle per 10 $m^3$). This is the same norm as used for viral vaccines that are based on viruses that are able to infect the host animal (like FMD). Pigs are not hosts for baculoviruses. The inactivated antigen bulk is stored at <–20° C. until it is formulated into a water-oil-water emulsion. A single dose containing 32 μg E2 (dose volume 2 ml) is sufficient to give protection (>PD95) against classical swine fever, from 2 weeks up to at least 6 months after vaccination. The production process is designed in such a way that scaling-up of the process is straightforward and use of 250L or even larger fermentors is possible. Scale-up of a static culture production is also straightforward; just use more tissue culture flasks. However, the total protein production routinely achieved in the 50 L fermentor would take approximately 7000 T175 tissue culture flasks. Cell growth and infection can be monitored and regulated better in a fermentor, since an oxygen and pH electrode are present. In tissue culture flasks, flask-to-flask variation is probably present, but it cannot be quantified. Inactivation is monitored and regulated much more accurately in the vessels than was done in the static culture production. Volumetric production levels of other proteins expressed in the BEVS (in our institute) also improve considerably if cells are grown with a method provided by the invention. For example, the yield of bovine FSH increased by a factor of 3–4 using a 10 L fermentor. Cells were co-infected at an MOI of 0.003 of each of 2 recombinant baculoviruses at a cell density of $1.1*10^6$ cells/ml. The yield of different E2 proteins of BVDV and of $E^{ms}$ proteins or BVDV and/or CSFV in suspension cultures in shake flasks increased three-fold. The method is also applicable to other recombinant proteins.

TABLE I

Viral antigen detection by the Immunofluorescence technique on cryostat sections of different tissues.

| Group | Animal no. | Lab no. | Tonsil | Spleen | Kidney | Ileum | Death d.p.c. |
|---|---|---|---|---|---|---|---|
| A. | 443 | 1 | – | – | – | – | 20 |
| 2 μE2 | 444 | 2 | – | – | – | – | 20 |
| | 445 | 3 | – | – | – | – | 20 |
| | 446 | 4 | – | – | – | – | 20 |
| | 447 | 5 | + | – | + | + | 9 |
| | 448 | 6 | – | – | – | – | 9 |
| | 449(S) | 7 | + | + | + | + | 20 |
| | 450(S) | 8 | + | + | + | + | 20 |

TABLE I-continued

Viral antigen detection by the Immunofluorescence technique on cryostat sections of different tissues.

| Group | Animal no. | Lab no. | Tonsil | Spleen | Kidney | Ileum | Death d.p.c. |
|---|---|---|---|---|---|---|---|
| B. | 435 | 9 | − | − | − | − | 20 |
| 8 µE2 | 436 | 10 | − | − | − | − | 20 |
| | 437 | 11 | − | − | − | − | 20 |
| | 438 | 12 | − | − | − | − | 20 |
| | 439 | 13 | − | − | − | − | 20 |
| | 440 | 14 | + | + | + | — | 18 |
| | 441(S) | 15 | + | + | + | + | 20 |
| | 442(S) | 16 | + | + | + | + | 20 |
| C. | 427 | 17 | − | − | − | − | 20 |
| 32 µg E2 | 428 | 18 | − | − | − | − | 20 |
| | 429 | 19 | − | − | − | − | 20 |
| | 430 | 20 | − | − | − | − | 20 |
| | 431 | 21 | − | − | − | − | 20 |
| | 432 | 22 | − | − | − | − | 20 |
| | 433(S) | 23 | − | − | − | − | 20 |
| | 434(S) | 24 | − | − | − | − | 20 |
| D. | 59 | 25 | + | + | + | + | 10 |
| | 60 | 26 | + | + | + | + | 1 |

− = no fluorescence detected
+ = fluorescence detected
— = no data
* = animals were slaughtered at the end of the experiment 20 dpc.

[0158] TABLE 2

Results of the Virus Neutralization Test

| Group | Animal no. | Lab no | \multicolumn{4}{c}{Days post-vaccination} |
|---|---|---|---|---|---|---|

| Group | Animal no. | Lab no | 0 | 14 | 21 | 41 (at death) |
|---|---|---|---|---|---|---|
| A. | 443 | 1 | <12.5 | 19 | 75 | >1600 |
| 2 µ E2 | 444 | 2 | <12 | <12 | 19 | >1600 |
| | 445 | 3 | <12 | <12 | <12 | >1600 |
| | 446 | 4 | <12.5 | <12.5 | 12 | >1600 |
| | 447 | 5 | <12.5 | <12.5 | 19 | <12.5 |
| | 448 | 6 | <12.5 | 19 | 37 | — |
| | 449(S) | 7 | <12.5 | <12.5 | <12.5 | <12.5 |
| | 450(S) | 8 | <12.5 | <12.5 | <12.5 | <12.5 |
| B. | 435 | 9 | <12.5 | <12.5 | 100 | >1600 |
| 8 µ E2 | 436 | 10 | <12.5 | <12.5 | 400 | >1600 |
| | 437 | 11 | <12.5 | 75 | 600 | >1600 |
| | 438 | 12 | <12.5 | 37 | 400 | >1600 |
| | 439 | 13 | <12.5 | 37 | 75 | >1600 |
| | 440 | 14 | <12.5 | <12.5 | 37 | 600 |
| | 441(S) | 15 | <12.5 | <12.5 | <12.5 | <12.5 |
| | 442(S) | 16 | <12.5 | <12.5 | <12.5 | <12.5 |
| C. | 427 | 17 | <12.5 | 50 | 150 | >1600 |
| 32 µg E2 | 428 | 18 | <12.5 | 37 | 600 | >1600 |
| | 429 | 19 | <12.5 | >1600 | 1200 | >1600 |
| | 430 | 20 | <12.5 | <12.5 | 50 | >1600 |
| | 431 | 21 | <12.5 | <12.5 | 800 | >1600 |
| | 432 | 22 | <12.5 | <12.5 | 800 | >1600 |
| | 433(S) | 23 | <12.5 | <12.5 | <12.5 | <12.5 |
| | 434(S) | 24 | <12.5 | <12.5 | <12.5 | <12.5 |
| D. | 59 | 25 | <12.5 | <12.5+ | <12.5 | + |
| | 60 | 26 | <12.5 | <12.5 | <12.5 | + |

— = no data

What is claimed is:

1. A method of producing an E2 subunit vaccine that includes a classical swine fever virus E2 protein without a transmembrane region, said method comprising: growing insect cells in growth medium in a culture vessel; infecting the cells with an inoculum of a recombinant baculovirus encoding said classical swine fever E2 protein without a transmembrane region having a multiplicity of infection of said cells of between 0.0001 and 0.01; incubating said cells until greater than about half of the cells show cytopathic effect; removing cellular material from said growth medium; and formulating the E2 subunit vaccine from said cellular material to confer protection against classical swine fever at the PD95 level after one single vaccination with one dose without being immunoaffinity purified.

2. The method of claim 1, wherein the cells infected at a density of $5 \times 10^5$ cells/ml to about $1.5 \times 10^6$ cells/ml.

3. The method of claim 1, wherein the multiplicity of infection is between 0.001 and 0.005.

4. The method of claim 3, wherein the multiplicity of infection is between 0.001 and 0.003.

5. The method of claim 1, wherein said removing cell material comprises removing said cell material when the final concentration of said E2 protein in said growth medium is between 100 µg/ml and 300µg/ml.

6. The method of claim 1, wherein said E2 subunit vaccine is formulated by including an adjuvant.

7. The method of claim herein said adjuvant comprises a double water-in-oil emulsion.

8. A method of producing an E2 subunit vaccine that includes a classical swine fever virus E2 protein without a transmembrane region, said method comprising: growing insect cells in growth medium in a culture vessel; infecting the cells at any time of infection with an inoculum of a recombinant baculovirus encoding said classical swine fever E2 protein without the transmembrane region having a multiplicity of infection of said cells of between 0.0001 and 0.01; incubating said cells until greater than about half of the cells show cytopathic effect; removing cellular material from said growth medium; and formulating the E2 subunit vaccine from said cellular material to confer protection against classical swine fever at the PD95 level after one single vaccination with one dose without being immunoaffinity purified.

9. The method of claim 8, wherein the cells are infected at a density of $5 \times 10^5$ cells/ml to about $1.5 \times 10^6$ cells/ml.

10. The method of claim 8, wherein the multiplicity of infection is between 0.001 and 0.005.

11. The method of claim 10, wherein the multiplicity of infection is between 0.001 and 0.003.

12. The method of claim 8, wherein said removing cell material comprises removing said cell material when the final concentration of said protein or fragments thereof in said growth medium is between 100 µg/ml and 300µg/ml.

13. The method of claim 8, wherein said E2 subunit vaccine is formulated by adding an adjuvant.

14. The method of claim 13, wherein said adjuvant comprises a double water-in-oil emulsion.

* * * * *

UNITED STATES PATENT AND TRADEMARK OFFICE
CERTIFICATE OF CORRECTION

PATENT NO.    : 6,555,346 B1
DATED         : April 29, 2003
INVENTOR(S)   : Dietmar Kretzdorn et al.

It is certified that error appears in the above-identified patent and that said Letters Patent is hereby corrected as shown below:

<u>Title page, Item [54] and Column 1, lines 1 and 2,</u>
Replace the title in its entirety with -- E2 SUBUNIT VACCINE COMPRISING RECOMBINANT PESTIVIRUS E2 PROTEIN --

<u>Title page,</u>
Item [56], References Cited, OTHER PUBLICATIONS,
"Radford, et al." reference, change "Insects" to -- Insect --
Item [57], ABSTRACT,
Line 17, change "µl" to -- µ/ml --

<u>Column 4,</u>
Lines 11-12, delete the spaces and indentation indicating a new paragraph <u>Column 6,</u>
Line 35, change "$E^{ms}$" to -- $E^{rns}$ --

<u>Column 7,</u>
Lines 12 and 43, change "$E^{ms}$" to -- $E^{rns}$ --

<u>Column 8,</u>
Lines 40-41, delete the spaces and indentation indicating a new paragraph
Lines 44 and 50, change "$E^{ms}$" to -- $E^{rns}$ --
Lines 52 and 54, change "$E^{ms}$" to -- $E^{rns}$ --

<u>Column 10,</u>
Lines 4 and 48, change "I" to -- 1 --
Lines 18, 23, 25, 28, 32 and 33, change "$E^{ms}$" to -- $E^{rns}$ --
Lines 35, 41, 46 and 55 change "$E^{ms}$" to -- $E^{rns}$ --

<u>Column 11,</u>
Line 24, change "106" to -- $10^6$ --
Line 27, change "SF900I" to -- SF900II --
Line 66, change "$TCID_5/$" to -- $TCID_{50}/$ --

<u>Column 12,</u>
Line 27, change "<-20°C" to -- ≤-20°C --
Line 33, change "SF90011" to -- SF900II --
Line 37, change "3" to -- <3 --
Line 44, change "red" to -- solution is stored --
Line 63, change "filing" to -- filling --

UNITED STATES PATENT AND TRADEMARK OFFICE
CERTIFICATE OF CORRECTION

PATENT NO. : 6,555,346 B1
DATED : April 29, 2003
INVENTOR(S) : Dietmar Kretzdorn et al.

It is certified that error appears in the above-identified patent and that said Letters Patent is hereby corrected as shown below:

Column 13,
Line 9, in the second box of the flow chart change "5 ml" to -- 15 ml --

Column 14,
Line 16, in the flow chart, before "cells" delete "the"

Column 18,
Lines 42 and 43, change "106" to -- $10^6$ --

Column 19,
Line 14, change "bFSHct" to -- bFSHα --
Line 17, change "$10^{8,}$" to -- $10^8$, --
Line 67, delete the period after "between,"

Column 20,
Line 9, insert a hyphen after "leucocyte"

Column 26,
Line 47, change "$E^{ms}$" to -- $E^{rns}$ --

Column 27,
Line 35, delete "[158]"

Column 28,
Line 28, change "herein" to -- 6, wherein --

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,555,346 B1  Page 1 of 1
APPLICATION NO. : 09/596105
DATED : April 29, 2003
INVENTOR(S) : Dietmar Kretzdorn et al.

It is certified that error appears in the above-identified patent and that said Letters Patent is hereby corrected as shown below:

In the claims:

| | | | |
|---|---|---|---|
| CLAIM 1, | COLUMN 28, | LINES 14, 15 | change "said cellular material" to --said growth medium-- |
| CLAIM 2, | COLUMN 28, | LINE 18, | change "the cells infected" to --the cells are infected-- |
| CLAIM 8, | COLUMN 28, | LINE 44, | change "said cellular material" to --said growth medium-- |
| CLAIM 12, | COLUMN 28, | LINES 55, 56 | change "wherein said removing cell material" to --wherein said removing cellular material-- |
| CLAIM 12, | COLUMN 28, | LINE 56, | change "comprises removing said cell material" to --comprises removing said cellular material-- |

Signed and Sealed this

Tenth Day of November, 2009

David J. Kappos
*Director of the United States Patent and Trademark Office*